United States Patent
Waldman et al.

(10) Patent No.: US 11,286,308 B2
(45) Date of Patent: *Mar. 29, 2022

(54) CELL BASED ANTI-CANCER COMPOSITIONS WITH REDUCED TOXICITY AND METHODS OF MAKING THE SAME

(71) Applicant: Thomas Jefferson University, Philadelphia, PA (US)

(72) Inventors: Scott A. Waldman, Philadelphia, PA (US); Adam E. Snook, Aston, PA (US); Michael S. Magee, Cambridge, MA (US)

(73) Assignee: Thomas Jefferson University, Philadelphia, PA (US)

( * ) Notice: Subject to any disclaimer, the term of this patent is extended or adjusted under 35 U.S.C. 154(b) by 125 days.

This patent is subject to a terminal disclaimer.

(21) Appl. No.: 16/236,249

(22) Filed: Dec. 28, 2018

(65) Prior Publication Data

US 2019/0135944 A1    May 9, 2019

Related U.S. Application Data

(62) Division of application No. 15/198,144, filed on Jun. 30, 2016, now Pat. No. 10,202,463, which is a division of application No. 14/215,549, filed on Mar. 14, 2014, now Pat. No. 9,393,268.

(60) Provisional application No. 61/791,791, filed on Mar. 15, 2013.

(51) Int. Cl.
| | |
|---|---|
| *A61K 35/17* | (2015.01) |
| *C07K 16/40* | (2006.01) |
| *C07K 14/725* | (2006.01) |
| *C12N 15/113* | (2010.01) |
| *C12N 5/0783* | (2010.01) |
| *A61K 47/68* | (2017.01) |
| *A61K 35/28* | (2015.01) |
| *A61K 31/713* | (2006.01) |
| *C07K 14/705* | (2006.01) |
| *C07K 14/735* | (2006.01) |
| *A61K 35/12* | (2015.01) |

(52) U.S. Cl.
CPC ............ *C07K 16/40* (2013.01); *A61K 31/713* (2013.01); *A61K 35/17* (2013.01); *A61K 35/28* (2013.01); *A61K 47/6871* (2017.08); *C07K 14/7051* (2013.01); *C07K 14/70521* (2013.01); *C07K 14/70535* (2013.01); *C12N 5/0636* (2013.01); *C12N 15/1138* (2013.01); *A61K 2035/124* (2013.01); *C07K 2317/622* (2013.01); *C07K 2319/02* (2013.01); *C07K 2319/03* (2013.01); *C07K 2319/70* (2013.01); *C12N 2310/14* (2013.01); *C12N 2320/32* (2013.01)

(58) Field of Classification Search
CPC combination set(s) only.
See application file for complete search history.

(56) References Cited

U.S. PATENT DOCUMENTS

| | | | | |
|---|---|---|---|---|
| 2011/0171240 A1* | 7/2011 | Hoon | ...................... | A61P 31/00 424/172.1 |
| 2012/0251509 A1* | 10/2012 | Waldman | ................ | A61K 35/17 424/93.21 |

OTHER PUBLICATIONS

Snook et al. (Cancer Research, 2009, 69:3537-3544).*
Snook et al. (Cancer Immunol Immunother, 2012, 61:713-723).*
Snook et al. (Immunol Res. 2011, 51:161-169).*

* cited by examiner

*Primary Examiner* — Laura B Goddard

(57) ABSTRACT

Isolated pluralities of T cells which recognize at least one epitope of an intestinal cancer antigen or CNS cancer antigen and pharmaceutical compositions comprising the same are disclosed. Methods of making a plurality of T cells that recognize at least one epitope of an intestinal cancer antigen or CNS cancer antigen are also disclosed. Methods of treating an individual who has been diagnosed with cancer of a mucosal tissue or preventing such cancer in an individual at elevated risk are disclosed as are nucleic acid molecules that comprise a nucleotide sequence that encode proteins that recognize at least one epitope of an intestinal cancer antigen or CNS cancer antigen and T cells comprising such nucleic acid molecules.

9 Claims, No Drawings

US 11,286,308 B2

CELL BASED ANTI-CANCER COMPOSITIONS WITH REDUCED TOXICITY AND METHODS OF MAKING THE SAME

CROSS-REFERENCE TO RELATED APPLICATIONS

This application is a Divisional Application of U.S. application Ser. No. 15/198,144 filed Jun. 30, 2016 and granted as U.S. Pat. No. 10,202,463 on Feb. 12, 2019, which is a Divisional Application of U.S. application Ser. No. 14/214,549 filed Mar. 14, 2014 and granted as U.S. Pat. No. 9,393,268 on Jul. 19, 2016, which claims priority to U.S. Provisional Application No. 61/791,791, filed Mar. 15, 2013, which is incorporated herein by reference in its entirety.

FIELD

The disclosure relates to compositions that comprise T cells that target antigens of intestinal cells or CNS cells and that have reduced dose-limiting toxicity, and to methods of making such compositions. Methods of using such compositions to protect individuals against cancer of intestinal cells or CNS cells that express the target antigen and methods for treating individuals with such cancers are provided.

BACKGROUND

Despite improvements and successes in therapy, cancer continues to claim the lives of numerous people worldwide. For example, colorectal cancer is the third most common cause of death from malignant disease in Western countries. Worldwide, it has been estimated there are at least half a million new cases of colorectal cancer each year.

Improvements in screening provide the opportunity to identify many individuals who have early stage cancer as well as many who do not have cancer but who are genetically predisposed to developing cancer and thus at an elevated risk of developing cancer. Moreover, because of improvements in treatment, there are numerous people who have either had cancer removed or in remission. Such people are at a risk of relapse or recurrence and so are also at an elevated risk of developing cancer.

Therapies in which T cells are isolated from a donor/individual, identified as being specific for a particular antigen, expanded ex vivo to obtain large numbers of such cell which are administered to the patient have been described. In some embodiments, the donor/individual and the patient are the same person and the cells and therapy are referred to as autologous. In some embodiments, the donor/individual and the patient are not the same person but the donor/individual is screened to identify them as having very similar combinations of alleles (matched) encoding major histocompatibility complex (MHC), classes I and II proteins, also referred to as human leukocyte antigens (HLA) and the cells and therapy are referred to as allogenic.

In addition to isolating and expanding populations of antigen-specific T cells by ex vivo culturing, the T cells may be modified after isolating and before expanding populations by having genetic material added to them that encodes proteins such as cytokines, for example IL-2.

Further, T cells may be isolated and modified by having genetic material encoding T cell receptors (TCRs) known to specifically bind to antigens. T cells may be modified by providing them with expressible forms of a T cell receptor (TCR) different from the endogenous TCR of the modified T cells. Such T cells bind to cells displaying the target of either TCR. After being modified the cells are cultured to expanded populations of exogenous-TCR expressing antigen-specific T cells by ex vivo culturing, Antigen specific TCRs and the genetic sequences that encode them may be routinely identified and isolated to produce the gene constructs used as starting material. Exogenous TCR refers to a TCR which is the product of expression of genetic material added to the cell by gene delivery techniques whether the genetic material is derived from T cells from the same individual who supplies the T cells or if the TCR coding sequences are derived from a different individual than the donor of T cell to which the TCR coding sequences are added.

To increase the number of T cells that specifically bind to the antigen, the donor may be administered a vaccine which induced an immune response in the individual that will include generation of populations of T cells in the individual that specifically bind to an antigen of the vaccine.

TCRs are membrane bound heterodimers consisting of an alpha ($\alpha$) and beta ($\beta$) chain, which associate with the membrane bound CD3 protein complex and the $\zeta$-chain (zeta chain) to form a TCR complex. The CD3 protein complex includes a CD3$\gamma$ chain, a CD3$\delta$ chain, and two CD3$\varepsilon$ chains.

Therapies are known in which immune cells isolated from a donor/individual are modified to express a fusion protein, referred to as Chimeric antigen receptor (CAR) that has an extracellular antigen binding domain and intracellular signaling domain that activates the cells. Following modification, the cells are expanded ex vivo to obtain large numbers of such cell which are administered to the patient have been described. As above, autologous refers to the donor and recipient of the cells being the same person. Allogenic refers to the donor and recipient of the cells being different people.

CAR-based immunotherapy, also referred to as T-bodies, has become an emerging modality for treating cancer. CARs are fusion receptors that comprise a domain which ructions to provide HLA-independent binding of cell surface target molecules and a signaling domain that can activate host immune cells of various types, typically peripheral blood T cells, which may include populations of cells referred to cytotoxic lymphocytes, cytotoxic T lymphocytes (CTLs), Natural Killer T cells (NKT) and Natural Killer cells (NK) or helper T cells That is, while typically being introduced into T cells, genetic material encoding CARs may be added to immune cells that are not T cell such as NK cells.

Essentially, most CARs are an immunoglobulin-derived antigen binding domain fused to a T cell signaling domain such as the CD3zeta signaling chain of the T cell receptor or a T-cell costimulatory signaling (e.g. CD28) domain linked to a T-cell chain such as CD3zeta chain or the gamma-signal-transducing subunit of the Ig Fc receptor complex. CARs direct the recombinant cells in which they are expressed to bind to and, in the case of recombinant cytotoxic lymphocytes, recombinant cytotoxic T lymphocytes (CTLs), recombinant Natural Killer T cells (NKT) and recombinant Natural Killer cells (NK), kill cells displaying the antibody-specified target.

In CARs, a particularly useful form of immunoglobulin derived antigen binding domain is provided as single chain chimeric receptors that are MHC-independent. The antigen-binding domain is typically derived from an antibody and the signaling domain is derived from a TCR. In some embodiments, the CAR consists of an extracellular single chain fragment of antibody variable region that provides antigen binding function fused to a transmembrane and cytoplasmic signaling domain such as CD3zeta chain or CD28 signal domain linked to CD3zeta chain. In some embodiments the signaling domain is linked to the antigen binding domain by a spacer or hinge. When the fragment of antibody variable region binds to the antigen it specifically recognizes, the signaling domain initiates immune cell activation. These recombinant cells that express membrane bound chimeric receptors having an extracellular antibody-derived antigen binding domain and intracellular domain derived from TCRs which perform signaling functions to stimulate lymphocytes. Some embodiments provides antibody-derived antigen binding domain is a single chain variable fragment (scFv) that includes antigen binding regions of the heavy and light chain variable regions of an antibody. A signaling domain may include a T-cell costimulatory signaling (e.g. CD28) domain and T-cell triggering chain (e.g. CD3zeta).

In some embodiments, CAR coding sequences are introduced ex vivo into cells, such as T cells from peripheral lymphocytes using routine in vitro gene transfer techniques and materials such a retroviral vectors. Following gene transfer, the recombinant cells are cultured to expand the number of recombinant cells which are administered to a patient. The recombinant cells will recognize and bind to cells displaying the antigen recognized by the extracellular antibody-derived antigen binding domain.

Developments and improvements include identification of various signaling domains, the identification of various immune cells which can be used, the further modified of the cells to co-express cytokines or anti-apoptotic genes to aid in their continued survival.

There is a need for improved methods of treating individuals suffering from cancer of intestinal cells or from cancer of CNS cells. There is a need for compositions useful to treat individuals suffering from such cancers. There is a need for improved methods of preventing a recurrence of such cancer in individuals who have been treated for such cancer. There is a need for compositions useful to prevent a recurrence of such cancers in individuals who have been treated for cancer of intestinal cells. There is a need for improved methods of preventing such cancer in individuals, particularly those who have been identified as having a genetic predisposition for such cancer. There is a need for improved methods of identifying compositions useful to treat and prevent cancer of intestinal cells or CNS cells in individuals. There is a need for improved methods of treating individuals suffering from such cancers. There is a need for compositions useful to treat individuals suffering such cancer.

SUMMARY

The present disclosure provides isolated plurality of T cells which recognize at least one epitope of an intestinal cancer antigen or CNS cancer antigen; wherein said T cell is modified to inhibit expression or activity of one or more proteins selected from the group consisting of: $\alpha_4\beta_7$ integrin and chemokine receptor 9 (CCR9).

In some embodiments, the T cells are derived from clonal expansion of T cells isolated from an individual. In some embodiments, the T cells are derived from clonal expansion of T cells which recognize at least one epitope of an intestinal cancer antigen or CNS cancer antigen that are isolated from an individual. In some embodiments, the T cells are derived from clonal expansion of T cells that are isolated from an individual and transformed with a nucleic acid molecule which encodes a CAR which binds to an intestinal cancer antigen or CNS cancer antigen. In some embodiments, the nucleic acid molecule encodes a T cell receptor that is isolated from a T cell which recognizes at least one epitope of an intestinal cancer antigen or CNS cancer antigen. In some embodiments, the CAR that binds to an intestinal cancer antigen or CNS cancer antigen comprises: a GCC specific scFv linked to a truncated CD28 extracellular domain to the intracellular part of the FcRIγ chain; a GCC specific scFv linked to a truncated CD28 extracellular domain to the intracellular part of the CD3zeta signaling chain; a GCC specific scFv linked to the intracellular part of the FcRIγ chain; or a GCC specific scFv linked to the intracellular part of the CD3zeta signaling chain. In some embodiments, the T cells recognize at least one epitope of an intestinal cancer antigen selected from the group consisting of guanylyl cyclase C, sucrase isomaltase, CEA, CDX1, and CDX2. In some embodiments, the isolated plurality of cells are modified to inhibit expression or activity of $\alpha_4\beta_7$ integrin. In some embodiments, the isolated plurality of T cells are modified to inhibit expression of $\alpha_4\beta_7$ integrin by providing the isolated plurality of cells with nucleic acid sequences selected from the group consisting of: nucleic acid sequences that express siRNA which inhibits expression of $\alpha_4\beta_7$ integrin, nucleic acid sequences that express microRNA which inhibits expression of $\alpha_4\beta_7$ integrin, and nucleic acid sequences that express antisense sequences which inhibit expression of $\alpha_4\beta_7$ integrin. In some embodiments, the isolated plurality of T cells are modified to inhibit activity of $\alpha_4\beta_7$ integrin by providing the isolated plurality of T cells with nucleic acid sequences selected from the group consisting of: nucleic acid sequences that encode decoy molecules which bind to $\alpha_4\beta_7$ integrin at the site $\alpha_4\beta_7$ integrin binds to MAdCAM-1, nucleic acid sequences that encode anti-$\alpha_4\beta_7$ integrin antibodies, nucleic acid sequences that express negative mutant form of $\alpha_4$ of $\alpha_4\beta_7$ integrin that binds to $\beta_7$ to produce an inactive integrin; nucleic acid sequences that express negative mutant form of $\beta_7$ of $\alpha_4\beta_7$ integrin that binds to $\alpha_4$ to produce an inactive integrin; nucleic acid sequences that encode a protein that competitive forms heterodimers with $\alpha_4$ of $\alpha_4\beta_7$ integrin to dimerize with $\beta_7$ and produce non-$\alpha_4\beta_7$ integrin heterodimers; nucleic acid sequences that encode a protein that competitive forms heterodimers with $\beta_7$ of $\alpha_4\beta_7$ integrin to dimerize with $\alpha_4$ and produce non-$\alpha_4\beta_7$ integrin heterodimers; and nucleic acid sequences that encode MAdCAM-1 which binds to $\alpha_4\beta_7$ integrin. In some embodiments, the isolated plurality of T cells are modified to inhibit expression or activity of CCR9. In some embodiments, the isolated plurality of T cells are modified to inhibit expression of CCR9 by providing the isolated plurality of I cells with nucleic acid sequences selected from the group consisting of: nucleic acid sequences that express siRNA which inhibits expression of CCR9, nucleic acid sequences that express microRNA which inhibits expression of CCR9, and nucleic acid sequences that express antisense sequences which inhibit expression of CCR9. In some embodiments, the isolated plurality of T cells are modified to inhibit activity of CCR9 by providing the isolated plurality of T cells with nucleic acid sequences selected from the group consisting of: nucleic acid sequences that encode decoy molecules which bind to CCR9 at the site CCR9 binds to CCL25, nucleic acid sequences that encode anti-CCR9 antibodies, nucleic acid sequences that express negative mutant form of CCR9; and nucleic acid sequences that encode CCL25 which binds to CCR9.

The present disclosure also provides pharmaceutical composition comprisings an isolated plurality of T cells described herein and a pharmaceutically acceptable carrier or diluent.

The present disclosure also provides methods of making a plurality of T cells that recognize at least one epitope of an intestinal cancer antigen or CNS cancer antigen, and are modified to inhibit expression or activity of one or more proteins selected from the group consisting of: $\alpha_4\beta_7$ integrin and chemokine receptor 9 (CCR9), the method comprising the steps of: isolating a sample from a cell donor that comprises at least one T cell that recognizes at least one epitope of an intestinal cancer antigen or CNS cancer antigen; identifying a T cell that recognize at least one epitope of an intestinal cancer antigen or CNS cancer antigen; transforming the T cell that recognize at least one epitope of an intestinal cancer antigen or CNS cancer antigen with an expressible form of nucleic acid molecule that inhibits expression or activity of one or more proteins selected from the group consisting of $\alpha_4\beta_7$ integrin and chemokine receptor 9 (CCR9); and culturing said T cell under conditions to promote its replication for a period sufficient to produce a plurality of T cells that recognize an intestinal cancer antigen or CNS cancer antigen, wherein the expressible form of the nucleic acid molecule that inhibits expression or activity of one or more proteins selected from the group consisting of: $\alpha_4\beta_7$ integrin and chemokine receptor 9 (CCR9) is expressed, and a plurality of T cells that recognize an intestinal cancer antigen or CNS cancer antigen and are modified to inhibit expression or activity of one or more proteins selected from the group consisting of: $\alpha_4\beta_7$ integrin and chemokine receptor 9 (CCR9) are produced.

In some embodiments, the cell donor is administered a vaccine comprising a protein that comprises at least one epitope of an intestinal cancer antigen or CNS cancer antigen or a nucleic acid encoding a protein that comprises at least one epi tope of an intestinal cancer antigen or CNS cancer antigen. In some embodiments, the cell donor is administered a vaccine comprising a protein that comprises at least one epitope of an intestinal cancer antigen or CNS cancer antigen and a CD4 epitope or a nucleic acid encoding a protein that comprises at least one epitope of an intestinal cancer antigen or CNS cancer antigen and a CD4 epitope. In some embodiments, the cell that recognize at least one epitope of an intestinal cancer antigen or CNS cancer antigen is a T cell that recognize at least one epitope of an intestinal cancer antigen or CNS cancer antigen selected from the group consisting of guanylyl cyclase C, sucrase isomaltase, CDX1, CDX2, mammoglobin, and small breast epithelial mucin. In some embodiments, the isolated plurality of T cells are modified to inhibit expression or activity of $\alpha_4\beta_7$ integrin. In some embodiments, the isolated plurality of T cells are modified to inhibit expression or activity of $\alpha_4\beta_7$ integrin by delivering to the isolated plurality of cells, expressible forms of nucleic acid sequences selected from the group consisting of: nucleic acid sequences that express siRNA which inhibits expression of $\alpha_4\beta_7$ integrin, nucleic acid sequences that express microRNA which inhibits expression of $\alpha_4\beta_7$ integrin, and nucleic acid sequences that express antisense sequences which inhibit expression of $\alpha_4\beta_7$ integrin. In some embodiments, the isolated plurality of T cells are modified to inhibit expression or activity of $\alpha_4\beta_7$ integrin by delivering to the isolated plurality of T cells, expressible forms of nucleic acid sequences selected from the group consisting of: nucleic acid sequences that encode decoy molecules which bind to $\alpha_4\beta_7$ integrin at the site $\alpha_4\beta_7$ integrin binds to MAdCAM-1; nucleic acid sequences that encode anti-$\alpha_4\beta_7$ integrin antibodies; nucleic acid sequences that express negative mutant form of $\alpha_4$ of $\alpha_4\beta_7$ integrin that binds to $\beta_7$ to produce an inactive integrin; nucleic acid sequences that express negative mutant form of $\beta_7$ of $\alpha_4\beta_7$ integrin that binds to $\alpha_4$ to produce an inactive integrin; nucleic acid sequences that encode a protein that competitive forms heterodimers with $\alpha_4$ of $\alpha_4\beta_7$ integrin to dimerize with $\beta_7$ and produce non-$\alpha_4\beta_7$ integrin heterodimers; nucleic acid sequences that encode a protein that competitive forms heterodimers with $\beta_7$ of $\alpha_4\beta_7$ integrin to dimerize with $\alpha_4$ and produce non-$\alpha_4\beta_7$ integrin heterodimers; and nucleic acid sequences that encode MAdCAM-1 which binds to $\alpha_4\beta_7$ integrin. In some embodiments, the isolated plurality of T cells are modified to inhibit expression or activity of CCR9. In some embodiments, the isolated plurality of T cells are modified to inhibit expression of CCR9 by providing the isolated plurality of T cells with nucleic acid sequences selected from the group consisting of: nucleic acid sequences that express siRNA which inhibits expression of CCR9, nucleic acid sequences that express microRNA which inhibits expression of CCR9, and nucleic acid sequences that express antisense sequences which inhibit expression of CCR9. In some embodiments, the isolated plurality of T cells are modified to inhibit activity of CCR9 by providing the isolated plurality of T cells with nucleic acid sequences selected from the group consisting of: nucleic acid sequences that encode decoy molecules which bind to CCR9 at the site CCR9 binds to CCL25; nucleic acid sequences that encode anti-CCR9 antibodies; nucleic acid sequences that express negative mutant form of CCR9; and nucleic acid sequences that encode CCL25 which binds to CCR9. In some embodiments, the cell donor is a patient diagnosed with cancer of mucosal tissue or a patient identified as being at an elevated risk to develop cancer of mucosal tissue. In some embodiments, the cell donor is a patient identified as being at an elevated risk to develop cancer of mucosal tissue. In some embodiments, the cell donor is a patient diagnosed with cancer of mucosal tissue. In some embodiments, the cell donor is a patient diagnosed with metastatic cancer of mucosal tissue.

The present disclosure also provides methods of making a plurality of T cells that recognize at least one epitope of an intestinal cancer antigen or CNS cancer antigen and are modified to inhibit expression or activity of one or more proteins selected from the group consisting of: $\alpha_4\beta_7$ integrin and chemokine receptor 9 (CCR9), the method comprising the steps of: a) isolating a sample from a cell donor that comprises at least one T cell; b) transforming the T cell with: i) an expressible form of nucleic acid sequence that encodes either a T cell receptor that recognizes at least one epitope of an intestinal cancer antigen or CNS cancer antigen, or a cancer mucosal antigen-binding membrane-bound fusion protein that comprises at least a functional fragment of an antibody that binds to at least one epitope of an intestinal cancer antigen or CNS cancer antigen, wherein upon expression the fusion protein is a membrane bound protein; and ii) an expressible form of nucleic acid molecule that inhibits expression or activity of one or more proteins selected from the group consisting of: $\alpha_4\beta_7$ integrin and chemokine receptor 9 (CCR9), and c) culturing said transformed T cell under conditions to promote its replication for a period sufficient to produce a plurality of T cells that recognize an intestinal cancer antigen or CNS cancer antigen and are modified to inhibit expression or activity of one or more proteins selected from the group consisting of: $\alpha_4\beta_7$ integrin and chemokine receptor 9 (CCR9), wherein said i) the nucleic acid sequences that encodes either a T cell receptor that recognizes at least one epitope of an intestinal cancer antigen or CNS cancer antigen, or a cancer mucosal antigen-binding membrane-bound fusion protein that comprises at least a functional fragment of an antibody that binds to at least one epitope of an intestinal cancer antigen or CNS cancer antigen, and ii) the nucleic acid molecule that inhibits expression or activity of one or more proteins selected from the group consisting of: $\alpha_4\beta_7$ integrin and chemokine receptor 9 (CCR9), are expressed in said cells.

In some embodiments, the T cell is transformed with a nucleic acid sequence that encodes a T cell receptor that recognizes at least one epitope of an intestinal cancer antigen or CNS cancer antigen. In some embodiments, the nucleic acid sequence that encodes a T cell receptor that recognizes at least one epitope of an intestinal cancer antigen or CNS cancer antigen is obtained by the steps of: administering a vaccine that comprises at least one epitope of an intestinal cancer antigen or CNS cancer antigen or a nucleic acid encoding a protein that comprises at least one epitope of an intestinal cancer antigen or CNS cancer antigen to a TCR gene donor, obtaining one or more T cells from the TCR gene donor, identifying a T cell comprises a T cell receptor that recognizes at least one epitope of an intestinal cancer antigen or CNS cancer antigen, isolating from the T cell a nucleic acid sequence that encodes T cell receptor that recognizes at least one epitope of an intestinal cancer antigen or CNS cancer antigen, and preparing an expression vector that comprises a nucleic acid sequence that encodes T cell receptor that recognizes at least one epitope of an intestinal cancer antigen or CNS cancer antigen. In some embodiments, the TCR gene donor is administered a vaccine comprising a protein that comprises at least one epitope of an intestinal cancer antigen or CNS cancer antigen and a CD4 epitope or a nucleic acid encoding a protein that comprises at least one epitope of an intestinal cancer antigen or CNS cancer antigen and a CD4 epitope. In some embodiments, the T cell is transformed with a nucleic acid sequence that encodes a cancer mucosal antigen-binding membrane-bound fusion protein that comprises at least a functional fragment of an antibody that binds to at least one epitope of an intestinal cancer antigen or CNS cancer antigen, wherein upon expression the fusion protein is a membrane bound protein. In some embodiments, the nucleic acid sequence that encodes the cancer mucosal antigen-binding membrane-bound fusion protein is obtained by the steps of: administering a vaccine that comprises at least one epitope of an intestinal cancer antigen or CNS cancer antigen or a nucleic acid encoding a protein that comprises at least one epitope of an intestinal cancer antigen or CNS cancer antigen to an antibody gene donor, obtaining one or more B cells from the antibody gene donor, identifying either a B cell that produces an antibody which recognize at least one epitope of an intestinal cancer antigen or CNS cancer antigen or a hybrid cell derived from a B cell that produces antibodies which recognize at least one epitope of an intestinal cancer antigen or CNS cancer antigen, isolating from the B cell a nucleic acid sequence that encodes the antibody that recognizes at least one epitope of an intestinal cancer antigen or CNS cancer antigen, making a chimeric gene that encodes a functional fragment of the antibody that recognizes at least one epitope of an intestinal cancer antigen or CNS cancer antigen and a protein sequences that renders the fusion protein a membrane bound protein and preparing an expression vector that comprises the chimeric gene. In some embodiments, the vaccinated donor is administered a vaccine comprising a protein that comprises at least one epitope of an intestinal cancer antigen or CNS cancer antigen and a CD4 epitope or a nucleic acid encoding a protein that comprises at least one epitope of an intestinal cancer antigen or CNS cancer antigen and a CD4 epitope. In some embodiments, the T cell that recognize at least one epitope of an intestinal cancer antigen or CNS cancer antigen is a T cell that recognize at least one epitope of an intestinal cancer antigen or CNS cancer antigen selected from the group consisting of guanylyl cyclase C, sucrase isomaltase, CDX1, CDX2, mammoglobin, and small breast epithelial mucin. In some embodiments, the cell donor is a patient diagnosed with cancer of mucosal tissue or a patient identified as being at an elevated risk to develop cancer of mucosal tissue. In some embodiments, the cell donor is a patient identified as being at an elevated risk to develop cancer of mucosal tissue. In some embodiments, the cell donor is a patient diagnosed with cancer of mucosal tissue. In some embodiments, the cell donor is a patient diagnosed with metastatic cancer of mucosal tissue. In some embodiments, the TCR gene donor or antibody gene donor is a patient diagnosed with cancer of mucosal tissue or a patient identified as being at an elevated risk to develop cancer of mucosal tissue. In some embodiments, the cell donor is a patient identified as being at an elevated risk to develop cancer of mucosal tissue. In some embodiments, the cell donor is a patient diagnosed with cancer of mucosal tissue. In some embodiments, the cell donor is a patient diagnosed with metastatic cancer of mucosal tissue. In some embodiments, the cell donor is the TCR gene donor or antibody gene donor. In some embodiments, the isolated plurality of T cells are modified to inhibit expression or activity of $\alpha_4\beta_7$ integrin. In some embodiments, the isolated plurality of T cells are modified to inhibit expression or activity of $\alpha_4\beta_7$ integrin by delivering to the isolated plurality of T cells, expressible forms of nucleic acid sequences selected from the group consisting of: nucleic acid sequences that express siRNA which inhibits expression of $\alpha_4\beta_7$ integrin, nucleic acid sequences that express microRNA which inhibits expression of $\alpha_4\beta_7$ integrin, and nucleic acid sequences that express antisense sequences which inhibit expression of $\alpha_4\beta_7$ integrin. In some embodiments, the isolated plurality of T cells are modified to inhibit expression or activity of $\alpha_4\beta_7$ integrin by delivering to the isolated plurality of T cells, expressible forms of nucleic acid sequences selected from the group consisting of: nucleic acid sequences that encode decoy molecules which bind to $\alpha_4\beta_7$ integrin at the site $\alpha_4\beta_7$ integrin binds to MAdCAM-1 nucleic acid sequences that encode anti-$\alpha_4\beta_7$ integrin antibodies, nucleic acid sequences that express negative mutant form of $\alpha_4$ of $\alpha_4\beta_7$ integrin that binds to $\beta_7$ to produce an inactive integrin; nucleic acid sequences that express negative mutant form of $\beta_7$ of $\alpha_4\beta_7$ integrin that binds to $\alpha_4$ to produce an inactive integrin; nucleic acid sequences that encode a protein that competitive forms heterodimers with $\alpha_4$ of $\alpha_4\beta_7$ integrin to dimerize with $\beta_7$ and produce non-$\alpha_4\beta_7$ integrin heterodimers, nucleic acid sequences that encode a protein that competitive forms heterodimers with $\beta_7$ of $\alpha_4\beta_7$ integrin to dimerize with $\alpha_4$ and produce non-$\alpha_4\beta_7$ integrin heterodimers, and nucleic acid sequences that encode MAdCAM-1 which binds to $\alpha_4\beta_7$ integrin. In some embodiments, the isolated plurality of T cells are modified to inhibit expression or activity of CCR9. In some embodiments, the isolated plurality of T cells are modified to inhibit expression of CCR9 by providing the isolated plurality of T cells with nucleic acid sequences selected from the group consisting of: nucleic acid sequences that express siRNA which inhibits expression of CCR9, nucleic acid sequences that express microRNA which inhibits expression of CCR9, and nucleic acid sequences that express antisense sequences which inhibit expression of CCR9. In some embodiments, the isolated plurality of T cells are modified to inhibit activity of CCR9 by providing the isolated plurality of cells with nucleic acid sequences selected from the group consisting of nucleic acid sequences that encode decoy molecules which bind to CCR9 at the site CCR9 binds to CCL25, nucleic acid sequences that encode anti-CCR9 antibodies, nucleic acid sequences that express negative mutant form of CCR9; and nucleic acid sequences that encode CCL25 which binds to CCR9.

The present disclosure also provides methods of treating an individual who has been diagnosed with cancer of a mucosal tissue comprising the step of administering to the individual an effective amount of a plurality of T cells which recognize at least one epitope of an intestinal cancer antigen or CNS cancer antigen produced by any of the methods described herein.

The present disclosure also provides methods of preventing cancer of a mucosal tissue in an individual identified as being at an elevated risk of developing cancer of a mucosal tissue comprising the step of administering to the individual an effective amount of a plurality of T cells which recognize at least one epitope of an intestinal cancer antigen or CNS cancer antigen produced by any of the methods described herein.

The present disclosure also provides methods of treating an individual who has been diagnosed with cancer of a mucosal tissue comprising the step of administering to the individual an effective amount of a plurality of T cells which recognize at least one epitope of an intestinal cancer antigen or CNS cancer antigen and have been modified to inhibit expression or activity of one or more proteins selected from the group consisting of: $\alpha_4\beta_7$ integrin and CCR9.

The present disclosure also provides methods of preventing cancer of a mucosal tissue in an individual identified as being at an elevated risk of developing cancer of a mucosal tissue comprising the step of administering to the individual an effective amount of a plurality of T cells which recognize at least one epitope of an intestinal cancer antigen or CNS cancer antigen and have been modified to inhibit expression or activity of one or more proteins selected from the group consisting of: $\alpha_4\beta_7$ integrin and CCR9.

In some embodiments, the I cells are derived from clonal expansion of T cells isolated from an individual. In some embodiments, the cells are derived from clonal expansion of T cells which recognize at least one epitope of an intestinal cancer antigen or CNS cancer antigen that are isolated from an individual. In some embodiments, the T cells are derived from clonal expansion of T cells that are isolated from an individual and transformed with a nucleic acid molecule which encodes a protein that recognizes at least one epitope of an intestinal cancer antigen or CNS cancer antigen, wherein the protein is expressed as a membrane bound protein such that the T cells recognize at least one epitope of an intestinal cancer antigen or CNS cancer antigen. In some embodiments, the nucleic acid molecule encodes a T cell receptor that isolated from a T cell which recognizes at least one epitope of an intestinal cancer antigen or CNS cancer antigen. In some embodiments, the nucleic acid molecule encodes a cancer mucosal antigen-binding membrane-bound fusion protein which comprises at least a functional antigen binding fragments of an antibody which recognizes at least one epitope of an intestinal cancer antigen or CNS cancer antigen. In some embodiments, wherein the T cells that recognizes at least one epitope of an intestinal cancer antigen or CNS cancer antigen selected from the group consisting of guanylyl cyclase C, sucrase isomaltase, CDX1, CDX2, mammoglobin, and small breast epithelial mucin.

The present disclosure also provides isolated plurality of T cells which recognize at least one epitope of an antigen associated with cell of the central nervous system (CNS); wherein said T cell is modified to inhibit expression or activity of $\alpha_4$ integrins.

In some embodiments, the T cells are derived from clonal expansion of T cells isolated from an individual. In some embodiments, the T cells are derived from clonal expansion of T cells which recognize at least one epitope of an antigen associated with cell of the central nervous system (CNS) that are isolated from an individual. In some embodiments, the T cells are derived from clonal expansion of T cells that are isolated from an individual and transformed with a nucleic acid molecule which encodes a membrane-bound fusion protein that binds to an epitope of an antigen associated with cell of the central nervous system (CNS). In some embodiments, the nucleic acid molecule encodes a T cell receptor that isolated from a T cell which recognizes at least one epitope of an antigen associated with cell of the central nervous system (CNS). In some embodiments, the membrane-bound fusion protein that binds to an antigen associated with cell of the central nervous system (CNS) is encoded by the nucleic acid molecule comprises at least a functional antigen binding fragment of an antibody which recognizes at least one epitope of an antigen associated with cell of the central nervous system (CNS). In some embodiments, the isolated plurality of T cells are modified to inhibit expression or activity of $\alpha_4$ subunit of $\alpha_4$ integrins by providing the isolated plurality of T cells with nucleic acid sequences selected from the group consisting of: nucleic acid sequences that express siRNA which inhibits expression of $\alpha_4$ subunit of $\alpha_4$ integrins, nucleic acid sequences that express microRNA which inhibits expression of $\alpha_4$ subunit of $\alpha_4$ integrins, and nucleic acid sequences that express antisense sequences which inhibit expression of $\alpha_4$ subunit of $\alpha_4$ integrins. In some embodiments, the isolated plurality of T cells are modified to inhibit activity of $\alpha_4$ integrins by providing the isolated plurality of T cells with nucleic acid sequences selected from the group consisting of: nucleic acid sequences that encode decoy molecules which bind to an $\alpha_4$ integrin at the site an $\alpha_4$ integrin binds to its ligand; nucleic acid sequences that encode antibodies that bind to $\alpha_4$ subunit of $\alpha_4$ integrin; nucleic acid sequences that express negative mutant form of $\alpha_4$ produce inactive $\alpha_4$ integrins; nucleic acid sequences that encode a protein that competes with $\alpha_4$ to forms $\alpha_4$ integrin heterodimers; and nucleic acid sequences that encode ligands of $\alpha_4$ integrins.

The present disclosure also provides pharmaceutical compositions comprising an isolated plurality of T cells described herein and a pharmaceutically acceptable carrier or diluent.

The present disclosure also provides methods of making a plurality of T cells that recognize at least one epitope of an antigen associated with CNS cells and are modified to inhibit expression or activity of $\alpha_4$ integrins, the method comprising the steps of isolating a sample from a cell donor that comprises at least one T cell that recognizes at least one epitope of an antigen associated with CNS cells; identifying a T cell that recognize at least one epitope of an antigen associated with CNS cells; transforming the T cell that recognize at least one epitope of an antigen associated with CNS cells with an expressible form of nucleic acid molecule that inhibits expression or activity $\alpha_4$ integrins; and culturing said cell under conditions to promote its replication for a period sufficient to produce a plurality of T cells that recognize an antigen associated with CNS cells, wherein the expressible form of the nucleic acid molecule that inhibits expression or activity of $\alpha_4$ integrins is expressed, and a plurality of T cells that recognize of an antigen associated with CNS cells and are modified to inhibit expression or activity of $\alpha_4$ integrins are produced.

In some embodiments, the cell donor is administered a vaccine comprising a protein that comprises at least one epitope of an antigen associated with CNS cells, or a nucleic acid encoding a protein that comprises at least one epitope of an antigen associated with CNS cells. In some embodiments, the cell donor is administered a vaccine comprising a protein that comprises at least one epitope of an antigen associated with CNS cells and a CD4 epitope or a nucleic acid encoding a protein that comprises at least one epitope of an antigen associated with CNS cells and a CD4 epitope. In some embodiments, the isolated plurality of T cells are modified to inhibit expression or activity of $\alpha_4$ subunit of $\alpha_4$ integrins by providing the isolated plurality of T cells with nucleic acid sequences selected from the group consisting of: nucleic acid sequences that express siRNA which inhibits expression of $\alpha_4$ subunit of $\alpha_4$ integrins, nucleic acid sequences that express microRNA which inhibits expression of $\alpha_4$ subunit of $\alpha_4$ integrins, and nucleic acid sequences that express antisense sequences which inhibit expression of $\alpha_4$ subunit of $\alpha_4$ integrins. In some embodiments, the isolated plurality of T cells are modified to inhibit activity of $\alpha_4$ integrins by providing the isolated plurality of T cells with nucleic acid sequences selected from the group consisting of: nucleic acid sequences that encode decoy molecules which bind to an a integrin at the site an $\alpha_4$ integrin binds to its ligand, nucleic acid sequences that encode antibodies that bind to $\alpha_4$ subunit of $\alpha_4$ integrin, nucleic acid sequences that express negative mutant form of $\alpha_4$ produce inactive $\alpha_4$ integrins; nucleic acid sequences that encode a protein that competes with $\alpha_4$ to forms integrin heterodimers, and nucleic acid sequences that encode ligands of $\alpha_4$ integrins. In some embodiments, the cell donor is a patient diagnosed with cancer of mucosal tissue or a patient identified as being at an elevated risk to develop cancer of a CNS cell. In some embodiments, the cell donor is a patient identified as being at an elevated risk to develop cancer of a CNS cell. In some embodiments, the cell donor is a patient diagnosed with cancer of a CNS cell. In some embodiments, the cell donor is a patient diagnosed with metastatic cancer of a CNS cell.

The present disclosure also provides methods of making a plurality of T cells that recognize at least one epitope of an antigen associated with CNS cells and are modified to inhibit expression or activity of $\alpha_4$ integrins, the method comprising the steps of: a) isolating a sample from a cell donor that comprises at least one T cell; b) transforming the T cell with: i) an expressible form of nucleic acid sequence that encodes either a T cell receptor that recognizes at least one epitope of an antigen associated with CNS cells, or a membrane bound fusion protein that comprises at least a functional fragment of an antibody that binds to at least one epitope of an antigen associated with CNS cells, wherein upon expression the fusion protein is a membrane bound protein; and ii) an expressible form of nucleic acid molecule that inhibits expression or activity of $\alpha_4$ integrins, and c) culturing said transformed T cell under conditions to promote its replication for a period sufficient to produce a plurality of T cells that recognize an antigen associated with CNS cells and are modified to inhibit expression or activity of $\alpha_4$ integrins, wherein said i) the nucleic acid sequences that encodes either a T cell receptor that recognizes at least one epitope of an antigen associated with CNS cells, or a membrane-bound fusion protein that comprises at least a functional fragment of an antibody that binds to at least one epitope of an antigen associated with CNS cells, and ii) the nucleic acid molecule that inhibits expression or activity of $\alpha_4$ integrins, are expressed in said cells.

In some embodiments, the T cell is transformed with a nucleic acid sequence that encodes a T cell receptor that recognizes at least one epitope of an antigen associated with CNS cells. In some embodiments, the nucleic acid sequence that encodes a T cell receptor that recognizes at least one epitope of an antigen associated with CNS cells is obtained by the steps of: administering a vaccine that comprises at least one epitope of an antigen associated with CNS cells or a nucleic acid encoding a protein that comprises at least one epitope of an antigen associated with CNS cells to a TCR gene donor, obtaining one or more T cells from the TCR gene donor, identifying a T cell comprises a T cell receptor that recognizes at least one epitope of an antigen associated with CNS cells, isolating from the T cell a nucleic acid sequence that encodes T cell receptor that recognizes at least one epitope of an antigen associated with CNS cells, and preparing an expression vector that comprises a nucleic acid sequence that encodes T cell receptor that recognizes at least one epitope of an antigen associated with CNS cells. In some embodiments, the TCR gene donor is administered a vaccine comprising a protein that comprises at least one epitope of an antigen associated with CNS cells and a CD4 epitope or a nucleic acid encoding a protein that comprises at least one epitope of an antigen associated with CNS cells and a CD4 epitope. In some embodiments, the cell is transformed with a nucleic acid sequence that encodes a cancer mucosal antigen-binding membrane-bound fusion protein that comprises at least a functional fragment of an antibody that binds to at least one epitope of an intestinal cancer antigen or CNS cancer antigen, wherein upon expression the fusion protein is a membrane bound protein. In some embodiments, the nucleic acid sequence that encodes the membrane-bound fusion protein that binds to an antigen associated with CNS cells is obtained by the steps of: administering a vaccine that comprises at least one epitope of an antigen associated with CNS cells or a nucleic acid encoding a protein that comprises at least one epitope of an antigen associated with CNS cells to an antibody gene donor, obtaining one or more B cells from the antibody gene donor, identifying either a B cell that produces an antibody which recognize at least one epitope of an antigen associated with CNS cells or a hybrid cell derived from a B cell that produces antibodies which recognize at least one epitope of an antigen associated with CNS cells, isolating from the B cell a nucleic acid sequence that encodes the antibody that recognizes at least one epitope of an antigen associated with CNS cells, making a chimeric gene that encodes a functional fragment of the antibody that recognizes at least one epitope of an antigen associated with CNS cells and a protein sequences that renders the fusion protein a membrane bound protein, and preparing an expression vector that comprises the chimeric gene. In some embodiments, the vaccinated donor is administered a vaccine comprising a protein that comprises at least one epitope of an antigen associated with CNS cells and a CD4 epitope or a nucleic acid encoding a protein that comprises at least one epitope of an antigen associated with CNS cells and a CD4 epitope. In some embodiments, the cell donor is a patient diagnosed with cancer of a CNS cell or a patient identified as being at an elevated risk to develop cancer of CNS cell. In some embodiments, the cell donor is a patient identified as being at an elevated risk to develop cancer of a CNS sell. In some embodiments, the cell donor is a patient diagnosed with cancer of a CNS cell. In some embodiments, the cell donor is a patient diagnosed with metastatic cancer of a CNS cell. In some embodiments, the TCR gene donor or antibody gene donor is a patient diagnosed with cancer of a CNS cell or a patient identified as being at an elevated risk to develop cancer of a CNS cell. In some embodiments, the cell donor is a patient identified as being at an elevated risk to develop cancer of a CNS cell. In some embodiments, the cell donor is a patient diagnosed with cancer of a CNS cell. In some embodiments, the cell donor is a patient diagnosed with metastatic cancer of a CNS cell. In some embodiments, the cell donor is the TCR gene donor or antibody gene donor. In some embodiments, the isolated plurality of T cells are modified to inhibit expression or activity of $\alpha_4$ subunit of $\alpha_4$ integrins by providing the isolated plurality of T cells with nucleic acid sequences selected from the group consisting of: nucleic acid sequences that express siRNA which inhibits expression of $\alpha_4$ subunit of $\alpha_4$ integrins, nucleic acid sequences that express microRNA which inhibits expression of $\alpha_4$ subunit of $\alpha_4$ integrins, and nucleic acid sequences that express antisense sequences which inhibit expression of $\alpha_4$ subunit of $\alpha_4$ integrins. In some embodiments, the isolated plurality of T cells are modified to inhibit activity of $\alpha_4$ integrins by providing the isolated plurality of T cells with nucleic acid sequences selected from the group consisting of: nucleic acid sequences that encode decoy molecules which bind to an $\alpha_4$ integrin at the site an $\alpha_4$ integrin binds to its ligand, nucleic acid sequences that encode antibodies that bind to $\alpha_4$ subunit of $\alpha_4$ integrin, nucleic acid sequences that express negative mutant form of $\alpha_4$ produce inactive $\alpha_4$ integrins; nucleic acid sequences that encode a protein that competes with $\alpha_4$ to forms $\alpha_4$ integrin heterodimers, and nucleic acid sequences that encode ligands of $\alpha_4$ integrins.

The present disclosure also provides methods of treating an individual who has been diagnosed with cancer of a CNS cell comprising the step of administering to the individual an effective amount of a plurality of T cells which recognize at least one epitope of an antigen of a CNS cell produced by any of the methods described herein.

The present disclosure also provides methods of preventing cancer of a mucosal tissue in an individual identified as being at an elevated risk of developing cancer of a CNS cell comprising the step of administering to the individual an effective amount of a plurality of cells which recognize at least one epitope of an antigen of associated with a CNS cell produced by any of the methods described herein.

The present disclosure also provides methods of treating an individual who has been diagnosed with cancer of a CNS cell comprising the step of administering to the individual an effective amount of a plurality of cells which recognize at least one epitope of an antigen of a CNS cell and have been modified to inhibit expression or activity of $\alpha_4$ integrins.

The present disclosure also provides methods of preventing cancer of a mucosal tissue in an individual identified as being at an elevated risk of developing cancer of a CNS cell comprising the step of administering to the individual an effective amount of a plurality of T cells which recognize at least one epitope of an antigen associated with a CNS cell and have been modified to inhibit expression or activity of $\alpha_4$ integrins.

In some embodiments, the T cells are derived from clonal expansion of T cells isolated from an individual. In some embodiments, the T cells are derived from clonal expansion of T cells which recognize at least one epitope of an antigen associated with a CNS cell that are isolated from an individual. In some embodiments, the T cells are derived from clonal expansion of T cells that are isolated from an individual and transformed with a nucleic acid molecule which encodes a protein that recognizes at least one epitope of an antigen associated with a CNS cell, wherein the protein is expressed as a membrane bound protein such that the T cells recognize at least one epitope of an antigen associated with a CNS cell. In some embodiments, the nucleic acid molecule encodes a T cell receptor that isolated from a T cell which recognizes at least one epitope of an antigen associated with a CNS cell. In some embodiments, the nucleic acid molecule encodes a membrane-bound fusion protein which binds to an antigen associated with a CNS cell that comprises at least a functional antigen binding fragments of an antibody which recognizes at least one epitope of an antigen associated with a CNS cell.

DETAILED DESCRIPTION

Definitions

As used herein, "an intestinal antigen" refers to an antigen that is expressed by cells that make up the intestine including the duodenum, small intestine, large intestine, colon and/or rectum and expressly excludes $\alpha_4\beta_7$ intergin and CCR9. An intestinal antigen may also be expressed by cells that make up tissue and organs other than the duodenum, small intestine, large intestine, colon and/or rectum. Examples of intestinal antigens include but are not limited to guanylyl cyclase C (GCC), CDX-1, CDX-2 and sucrase isomaltase.

As used herein, "a CNS antigen" refers to an antigen that is expressed by cells that make up the central nervous system including the brain, the spinal column including the spinal canal that contains the cerebral spinal fluid and neurons and expressly excludes $\alpha_4$ integrins.

As used herein, the term "CNS" refers to the brain, the spinal canal that contains cerebral spinal fluid and neurons.

As used herein, "CNS cancer" refers to cancer originating from brain cells, the cells of the spinal canal that contains cerebral spinal fluid and neurons.

As used herein, "colorectal cancer" refers to cancer of the intestine including cancer of the duodenum, cancer of the small intestine, cancer of the large intestine, cancer of the colon and/or cancer of the rectum.

As used herein, "an individual is suspected of being susceptible to cancer of colorectal cancer" is meant to refer to an individual who is at an above-average risk of developing colorectal cancer. Examples of individuals at a particular risk of developing colorectal cancer are those whose family medical history indicates above average incidence of colorectal cancer among family members and/or those who have genetic markers whose presence is correlatively for elevated incidence of colorectal cancer and/or those who have already developed cancer of colorectal tissue and have been treated who therefore face a risk of disease progression, relapse or recurrence. Factors which may contribute to an above-average risk of developing cancer of colorectal tissue which would thereby lead to the classification of an individual as being suspected of being susceptible to colorectal cancer may be based upon an individual's specific genetic, medical and/or behavioral background and characteristics.

As used herein, "an individual is suspected of being susceptible to CNS cancer" is meant to refer to an individual who is at an above-average risk of developing CNS cancer. Examples of individuals at a particular risk of developing CNS cancer are those whose family medical history indicates above average incidence of CNS cancer among family members and/or those who have genetic markers whose presence is correlatively for elevated incidence of CNS cancer and/or those who have already developed CNS cancer and have been treated who therefore face a risk of disease progression, relapse or recurrence. Factors which may contribute to an above-average risk of developing CNS cancer which would thereby lead to the classification of an individual as being suspected of being susceptible to CNS cancer may be based upon an individual's specific genetic, medical and/or behavioral background and characteristics.

As used herein the term "isolated plurality of cells" refers to a population of at least $1\times10^6$ cells maintained outside a living organism. In some embodiments, the isolated plurality of cells comprises a population of at least $1\times10^7$ cells maintained outside a living organism. In some embodiments, the isolated plurality of cells comprises a population of at least $1\times10^8$ cells maintained outside a living organism. In some embodiments, the isolated plurality of cells comprises a population of at least $1\times10^9$ cells maintained outside a living organism. In some embodiments, the isolated plurality of cells comprises a population of at least $1\times10^{10}$ cells maintained outside a living organism. In some embodiments, the isolated plurality of cells comprises a population of at least $1\times10^{11}$ such cells maintained outside a living organism. A population may be maintained in multiple containers or a single container.

As used herein the term "isolated plurality of T cells that recognizes at least one epitope of an intestinal antigen" and "isolated plurality of T cells that recognizes at least one epitope of an intestinal antigen" refers to a population of at least $1\times10^6$ T cells maintained outside a living organism which are each reactive to at least one epitope of an intestinal antigen. In some embodiments, the isolated plurality of T cells comprises a population of at least $1\times10^7$ such T cells maintained outside a living organism. In some embodiments, the isolated plurality of T cells comprises a population of at least $1\times10^8$ such T cells maintained outside a living organism. In some embodiments, the isolated plurality of T cells comprises a population of at least $1\times10^9$ such T cells maintained outside a living organism. In some embodiments, the isolated plurality of T cells comprises a population of at least $1\times10^{10}$ such T cells maintained outside a living organism. In some embodiments, the isolated plurality of T cells comprises a population of at least $1\times10^{11}$ such T cells maintained outside a living organism. A population may be maintained in multiple containers or a single container.

As used herein the term "isolated plurality of T cells that recognizes at least one epitope of a CNS antigen" refers to a population of at least $1\times10^6$ cells maintained outside a living organism which are each reactive to at least one epitope of a CNS antigen. In some embodiments, the isolated plurality of T cells comprises a population of at least $1\times10^7$ such T cells maintained outside a living organism. In some embodiments, the isolated plurality of T cells comprises a population of at least $1\times10^8$ such T cells maintained outside a living organism. In some embodiments, the isolated plurality of T cells comprises a population of at least $1\times10^9$ such T cells maintained outside a living organism. In some embodiments, the isolated plurality of T cells comprises a population of at least $1\times10^{10}$ such T cells maintained outside a living organism. In some embodiments, the isolated plurality of T cells comprises a population of at least $1\times10^{11}$ such T cells maintained outside a living organism. A population may be maintained in multiple containers or a single container.

As used herein the term "at least one epitope of an intestinal antigen" is meant to refer to a molecule that is immunologically cross reactive with an intestinal antigen including the full length intestinal antigen and fragments thereof.

As used herein the term "at least one epitope of a CNS antigen" is meant to refer to a molecule that is immunologically cross reactive with a CNS antigen including the full length CNS antigen and fragments thereof.

As used herein the term "an intestinal antigen-binding membrane bound fusion protein" refers to a protein comprises at least a functional fragment of an antibody that recognizes at least one epitope of an intestinal antigen and a portion which causes the protein, when expressed in a cell, to be a membrane bound protein.

As used herein the terms "a CNS antigen-binding membrane bound fusion protein" and "a membrane bound fusion protein that binds to an antigen associated with a CNS cell" refers to a protein comprises at least a functional fragment of an antibody that recognizes at least one epitope of a CNS antigen and a portion which causes the protein, when expressed in a T cell, to be a membrane bound protein.

As used herein, "a CD4+ helper epitope" is peptide sequence that forms a complex with a Major Histocompatibility Complex (MHC) Class 2 human leukocyte antigen (HLA) and is recognized by T cell receptors on CD4+ T cells. A peptide, e.g. CD4+ helper epitope, forms a complex with an MHC and this complex may be recognized by a particular T cell receptor. The interaction between the MHC/peptide complex and the cell receptor results in signals between the cell expressing the MHC and the T cell expressing the T cell receptor. In the case of the MHC class II, the complex formed by the peptide and MHC class II complex interacts with T cell receptors of CD4+ helper T cells. Thus, a peptide which can form a complex with an MHC class II molecule that can be recognized as a complex by a T cell receptor of a CD4+ helper T cell is a CD4+ helper epitope.

As used herein, "a secretion signal" and "a secretion peptide" and "a signal peptide" are used interchangeably and meant to refer to an amino acid sequence of a protein which when present results in the transportation and secretion of the protein to the exterior of the cell. Secretion signals are typically cleavable hydrophobic segments of a precursor protein at or near the N terminus of the precursor protein. In the secretion process, such secretion signals are enzymatically removed to result in the secretion of a mature form of the protein, i.e. a form of the protein lacking the secretion signal. In some embodiments, the secretion signal is derived from an intestinal antigen. In some embodiments, the secretion signal is derived from a CNS antigen. In some embodiments, the secretion signal is derived from another source. In some embodiments, the coding sequence of the intestinal antigen including the signal sequence is used intact. In some embodiments, a nucleotide sequence encoding the signal sequence from another source is linked the coding sequence of the intestinal antigen. In some embodiments, the coding sequence of the CNS antigen including the signal sequence is used intact. In some embodiments, a nucleotide sequence encoding the signal sequence from another source is linked the coding sequence of the CNS antigen. The signal sequence may be any such sequence which is functional in the cells of the individual to whom the genetic construct is administered.

Overview

Immune cells such as T cells express various adhesion molecules and chemokines on their surface. These adhesion molecules and chemokines have ligands or binding partners to which the adhesion molecules and chemokines are attracted and attach or bind to. Integrins are a type of adhesion molecule. The distribution of ligands or binding partners in various tissues results in immune cells with particular adhesion molecules or chemokines trafficking to tissue which expressed the binding partner.

Integrins contain an α subunit and a β subunit. There are several forms of the α subunit and several versions of the β subunit.

Integrins which comprise the $\alpha_4$ form of the α subunit are referred to as $\alpha_4$ integrins. Immune cells that express $\alpha_4$ integrins traffic toward and among CNS cells which express the $\alpha_4$ integrin's ligand.

Integrins which comprise the $\alpha_4$ form of the α subunit and the $\beta_7$ form of the β subunit are referred to as $\alpha_4\beta_7$ integrin. Immune cells that express $\alpha_4\beta_7$ integrin traffic toward and among intestinal cells which express the $\alpha_4\beta_7$ integrin's ligand MAdCAM-1.

Chemokine receptor 9 (CCR9) is a form of chemokine. Immune cells that express CCR9 traffic toward and among intestinal cells which express the CCR9 ligand CCL25.

As discussed above, there are several different approaches to using immune cells as therapeutics which involve isolating cells and expanding the population ex vivo and administering the expanded population of cells to an individual. A common problem among these therapies is the unintended trafficking of the therapeutic population of immune cells trafficking to normal cells, tissues and organs which express ligands or binding partners of adhesion molecules and chemokines expressed by the expanded population of therapeutic cells. Specifically, an expanded population of therapeutic cells which are produced to treat intestinal cancer will traffick to normal intestinal cells if the cells of the expanded population of therapeutic cells express $\alpha_4\beta_7$ integrin or CCR9. The trafficking to normal intestinal cells of the therapeutic cells useful to treat intestinal cancer can have deleterious consequences. Likewise, an expanded population of therapeutic cells which are produced to treat CNS cancer will traffick to normal CNS cells if the cells of the expanded population of therapeutic cells express $\alpha_4$ integrins. The trafficking to normal CNS cells of the therapeutic cells useful to treat CNS cancer can have deleterious consequence.

Cells may be engineered to blockade their trafficking to sites where normal cells express such antigens, thereby making the cells particularly effective against cancer that expresses the antigen. Such cells would produce less side effects compared to similar cells not engineered to blockade their trafficking to sites where normal cells express such antigens.

Provided herein are cells and methods designed to inhibit expression or binding activity of $\alpha_4\beta_7$ integrin or CCR9 in therapeutic cells useful to treat intestinal cancer. Genetic alterations of such immune cells is provided herein to limit the level of or block the trafficking of such cells to tissues expressing the intestinal antigen for which the anti-intestinal antigen cell targets. In particular, anti-intestinal cells are provided for which trafficking to intestinal sites is blocked such that exposure of such tissue to the cells in reduced or eliminated, thereby minimizing side effects of anti-intestinal antigen cells that target antigens expressed by normal intestinal cells. As one example, in composition for and method of treating metastatic colorectal cancer, in which metastases typically reside in lymph nodes, lung, liver, brain and bone, using GCC-specific T cells or CEA-specific T cells, the trafficking of such T cells to normal intestinal cells may be limited by expression or binding activity of $\alpha_4\beta_7$ integrin or CCR9 thus preventing toxicity while allowing destruction of metastases in non-intestinal sites. Examples of intestinal antigens include but are not limited GCC, CEA, CDX1, CDX1 and sucrose isomaltase. In some embodiments, the intestinal antigens may be expressed only in the mucosa.

Provided herein are cells and methods designed to inhibit expression or binding activity of $\alpha_4$ integrins in therapeutic cells useful to treat CNS cancer. Genetic alterations of such immune cells is provided herein to limit the level of or block the trafficking of such cells to tissues expressing the CNS antigen for which the anti-CNS antigen cell targets. In particular, anti-intestinal cells are provided for which trafficking to intestinal sites is blocked such that exposure of such tissue to the cells in reduced or eliminated, thereby minimizing side effects of anti-intestinal antigen cells that target antigens expressed by normal intestinal cells.

Cells

As noted above, immune cells are typically peripheral blood T cells. The immune cells may include populations of cells referred to cytotoxic lymphocytes, cytotoxic T lymphocytes (CTLs), Natural Killer T cells (NKT) and Natural Killer cells (NK) or helper T cells In some embodiment, the cells are selected as being directed to intestinal cancer or CNS cancer. In some embodiment, the cells are T cells selected as being directed to intestinal cancer or CNS cancer by having TCRs which bind to antigens expressed by intestinal cells or CNS cells. Silencing $\alpha_4\beta_7$ integrin or CCR9 expression or inhibiting $\alpha_4\beta_7$ integrin or CCR9 binding activity in cells propagated to target intestinal cancer reduces trafficking of the cells to normal intestinal tissue. Silencing $\alpha_4$ integrin expression or inhibiting $\alpha_4$ integrin binding activity in cells propagated to target CNS cancer reduces trafficking of the cells to normal CNS tissue.

In some embodiment, the cells are genetically modified to express TCRs or CARs that bind to intestinal antigens or CNS to antigens. Silencing $\alpha_4\beta_7$ integrin or CCR9 expression or inhibiting $\alpha_4\beta_7$ integrin or CCR9 binding activity in cells propagated to target intestinal cancer reduces trafficking of the cells to normal intestinal tissue. Silencing $\alpha_4$ integrin expression or inhibiting $\alpha_4$ integrin binding activity in cells propagated to target CNS cancer reduces trafficking of the cells to normal CNS tissue.

In some embodiments, T cells are provided which recognize at least one epitope of an intestinal antigen such that these T cells will bind to cancer cells which express the intestinal antigen, and thereby immunologically react with and against the cancer cells. The T cells provided herein are altered, modified or otherwise engineered so that their trafficking to intestinal sites will be limited or blocked and thus side effects caused by the immune reaction of T cells which bind to normal intestinal cells which express the intestinal antigen are reduced or eliminated.

In some embodiments, T cells are provided which recognize at least one epitope of a CNS antigen such that these T cells will bind to cancer cells which express the CNS antigen, and thereby immunologically react with and against the cancer cells. The T cells provided herein are altered, modified or otherwise engineered so that their trafficking to CNS sites will be limited or blocked and thus side effects caused by the immune reaction of T cells which bind to normal CNS cells which express the CNS antigen are reduced or eliminated.

While not wishing to be limited to any particular method of making pluralities of immune cells, such as pluralities of T cells which recognize at least one epitope of an intestinal antigen, three methods are provided herein. A first way to obtain a plurality of immune cells, such as a plurality of T cells which recognize at least one epitope of an intestinal antigen, is to isolate an immune cell such as a T cell which recognize at least one epitope of an intestinal antigen and, using culturing techniques, exponentially expand the number of cells to produce a plurality of such cells. A second way to obtain a plurality of immune cells such as a plurality of T cells which recognize at least one epitope of an intestinal antigen is to isolate an immune cell such as a T cell from an individual, transform it with a nucleic acid molecule that encodes a T cell receptor which recognizes at least one epitope of an intestinal antigen and, using culturing techniques, exponentially expand the number of transformed cells to produce a plurality of such cells. A third way to obtain a plurality of immune cells such as T cells which recognize at least one epitope of an intestinal antigen is to isolate an immune cell such as a T cell from an individual, transform it with a nucleic acid molecule that encodes a CAR which recognize at least one epitope of an intestinal antigen. In each instance, the cells are modified to blockade their trafficking to intestinal cells.

These cells such as T cells are used as therapeutics and prophylactics against cancer that expresses the intestinal antigen, particularly for example metastatic cancer of intestinal origin, non-intestinal cancer that is derived from cells that normally express the intestinal antigen or cancer in which the intestinal antigen is not normally expressed but which when transformed comprises cancer cells that express the intestinal antigen.

In some embodiments, cells such as T cells are provided which recognize at least one epitope of an intestinal antigen such that these cells will bind to cancer cells which express the intestinal antigen, and thereby immunologically react with and against the cancer cells. The cells provided herein are modified so that their trafficking to intestinal sites will be limited and thus side effects caused by the immune reaction of cells which bind to normal intestinal cells which express the intestinal antigen are reduced or eliminated.

While not wishing to be limited to any particular method of making pluralities of immune cells, such as pluralities of T cells which recognize at least one epitope of a CNS antigen, three methods are provided herein. A first way to obtain a plurality of immune cells, such as a plurality of T cells which recognize at least one epitope of a CNS antigen, is to isolate an immune cell such as a T cell which recognize at least one epitope of an a CNS and, using culturing techniques, exponentially expand the number of cells to produce a plurality of such cells. A second way to obtain a plurality of immune cells such as a plurality of T cells which recognize at least one epitope of a CNS antigen is to isolate an immune cell such as a T cell from an individual, transform it with a nucleic acid molecule that encodes a T cell receptor which recognizes at least one epitope of a CNS antigen and, using culturing techniques, exponentially expand the number of transformed cells to produce a plurality of such cells. A third way to obtain a plurality of immune cells such as T cells which recognize at least one epitope of a CNS antigen is to isolate an immune cell such as a T cell from an individual, transform it with a nucleic acid molecule that encodes a CAR which recognize at least one epitope of a CNS antigen. In each instance, the cells are modified to blockade their trafficking to CNS cells.

These cells such as T cells are used as therapeutics and prophylactics against cancer that expresses the CNS antigen, particularly for example metastatic cancer of CNS non-CNS cancer that is derived from cells that normally express the CNS antigen or cancer in which the CNS antigen is not normally expressed but which when transformed comprises cancer cells that express the CNS antigen.

In some embodiments, cells such as T cells are provided which recognize at least one epitope of a CNS antigen such that these T cells will bind to cancer cells which express the CNS antigen, and thereby immunologically react with and against the cancer cells. The cells provided herein are modified so that their trafficking to CNS sites will be limited and thus side effects caused by the immune reaction of cells which bind to normal CNS cells which express the CNS antigen are reduced or eliminated.

Antigen Specific T Cells as Starting Material

Some embodiments provide the clonal expansion of a cell that recognizes at least one epitope of an intestinal antigen comprising isolating such a T cell from a cell donor and, using culturing techniques, exponentially expand the number of cells by maintaining them under conditions which promote cell division.

Some embodiments provide the clonal expansion of a T cell that recognizes at least one epitope of a CNS antigen comprising isolating such a T cell from a cell donor and, using culturing techniques, exponentially expand the number of cells by maintaining them under conditions which promote cell division.

In the case of T cells that recognize intestinal antigens and in the case of T cells that recognize CNS antigens, the cell donor may be the individual to whom the expanded population of cells will be administered, i.e. an autologous cell donor. Alternatively, the T cell may be obtained from a cell donor that is a different individual from the individual to whom the T cells will be administered, i.e. an allogenic T cell. If an allogenic T cell is used, it is preferred that the donor be type matched, that is identified as expressing the same or nearly the same set of leukocyte antigens as the recipient.

T cells may be obtained from a cell donor by routine methods including, for example, isolation from blood fractions, particularly the peripheral blood monocyte component, or from bone marrow samples.

Once T cells are obtained from the cell donor, a T cell which recognizes at least one epitope of an intestinal antigen or a T cell which recognizes at least one epitope of a CNS antigen may be identified and isolated from the sample using standard techniques. The protein that comprises at least one epitope of the intestinal antigen or the protein that comprises at least one epitope of the CNS antigen may be adhered to a solid support and contacted with the sample. T cells that remain on the surface after washing are then further tested to identify T cells that which recognize at least one epitope of the intestinal antigen or T cells that which recognize at least one epitope of the intestinal antigen, respectively. Affinity isolation methods such as columns, labeled protein that binds to the cells, cell sorter technology may also be variously employed. T cells that recognize at least one epitope of an intestinal antigen or cells that which recognize at least one epitope of the CNS antigen may also be identified by their reactivity in the presence of a protein with at least one epitope of the intestinal antigen or at least one epitope of the CNS antigen respectively.

Once a cell is identified as a T cell that recognizes at least one epitope of the intestinal antigen or tat least one epitope of the CNS antigen, it may be clonally expanded using tissue culture techniques with conditions that promote and maintain cell growth and division to produce an exponential number of identical cells. The expanded population of T cells may be collected for administration to a patient. Prior to administration of such T cells to patients, the T cells are genetically modified to block trafficking to sites that express the antigen. That is, prior to administration of anti-intestinal antigen T cells to patients, the T cells are genetically modified to block trafficking to sites that express the intestinal antigen; prior to administration of anti-CNS antigen T cells to patients, the T cells are genetically modified to block trafficking to sites that express the CNS antigen.

In some embodiments, the T cells are genetically modified to block the trafficking of the T cells and their progeny to the intestine prior to clonal expansion. In some embodiments, the T cells are genetically modified to block the trafficking of the T cells and their progeny to the intestine after clonal expansion. In some embodiments, the T cells are genetically modified to block the trafficking of the T cells and their progeny to the CNS prior to clonal expansion. In some embodiments, the T cells are genetically modified to block the trafficking of the T cells and their progeny to the CNS after clonal expansion. Examples of vaccines and vaccination methods that used may be used to induce T cells that comprise a T cell receptor which recognizes at least one epitope of an intestinal antigen include those disclosed herein and those disclosed in the patents and published patent applications that have been incorporated by reference herein.

In some embodiments, the cell donor is vaccinated prior to removal of a sample comprising T cells in order to induce an immune response, including a T cell immune response, against at least one epitope of an intestinal antigen or against at least one epitope of a CNS antigen. In some embodiments, the cell donor is vaccinated prior to removal of a sample comprising T cells in order to induce an immune response, including a T cell immune response, against at least one epitope of an intestinal antigen as part of a treatment which includes identifying and isolating a T cell that recognizes at least one epitope of an intestinal antigen, culturing the cell to expand the number of such cells, and administering a plurality of such cells to a recipient who may be the same individual as the vaccinated cell donor (autographic procedure) or a different individual from the vaccinated cell donor (allographic procedure) wherein the T cells are modified to block the trafficking of the T cells and their progeny to the intestine before or after expanding the number of T cells. In some embodiments, the cell donor is vaccinated prior to removal of a sample comprising T cells in order to induce an immune response, including a T cell immune response, against at least one epitope of a CNS antigen as part of a treatment which includes identifying and isolating a T cell that recognizes at least one epitope of a CNS antigen, culturing the cell to expand the number of such cells, and administering a plurality of such cells to a recipient who may be the same individual as the vaccinated cell donor (autographic procedure) or a different individual from the vaccinated cell donor (allographic procedure) wherein the T cells are modified to block the trafficking of the T cells and their progeny to the CNS before or after expanding the number of T cells. Examples of vaccines and vaccination methods that used may be used to induce T cells that comprise a T cell receptor which recognizes at least one epitope of a CNS antigen include those disclosed herein and those disclosed in the patents and published patent applications that have been incorporated by reference herein.

T Cells Transformed with Antigen-Specific T Cell Receptors

In some embodiments, a plurality of immune cells, such as T cells, which recognize at least one epitope of an intestinal antigen may be obtained by isolating a T cell from a cell donor, transforming it with a nucleic acid molecule that encodes a T cell receptor which recognizes at least one epitope of an intestinal antigen and, culturing the transformed cell to exponentially expand the number of transformed immune cells, such as T cells, to produce a plurality of such cells. In some embodiments, the immune cells, such as T cells, are genetically modified to block the trafficking to the intestine of the immune cells, such as T cells, and their progeny prior to transforming them with a nucleic acid molecule that encodes a T cell receptor which recognizes at least one epitope of an intestinal antigen. In some embodiments, the immune cells, such as T cells, are genetically modified to block the trafficking to the intestine of the immune cells, such as T cells, and their progeny after transforming them with a nucleic acid molecule that encodes a T cell receptor which recognizes at least one epitope of an intestinal antigen. In some embodiments, the immune cells, such as T cells, are genetically modified to block the trafficking to the intestine of the immune cells, such as T cells, and their progeny prior to clonal expansion. In some embodiments, the immune cells, such as T cells, are genetically modified to block the trafficking to the intestine of the immune cells, such as T cells, and their progeny after to clonal expansion.

In some embodiments, a plurality of immune cells, such as T cells, which recognize at least one epitope of a CNS antigen may be obtained by isolating immune cells, such as T cells, from a cell donor, transforming it with a nucleic acid molecule that encodes a T cell receptor which recognizes at least one epitope of a CNS antigen and, culturing the transformed cell to exponentially expand the number of transformed immune cells, such as T cells, to produce a plurality of such cells. In some embodiments, the immune cells, such as T cells, are genetically modified to block the trafficking to the CNS of the immune cells, such as T cells, and their progeny prior to transforming them with a nucleic acid molecule that encodes a T cell receptor which recognizes at least one epitope of a CNS antigen. In some embodiments, the immune cells, such as T cells, are genetically modified to block the trafficking to the CNS of the immune cells, such as cells, and their progeny after transforming them with a nucleic acid molecule that encodes a T cell receptor which recognizes at least one epitope of a CNS antigen. In some embodiments, the immune cells, such as T cells, are genetically modified to block the trafficking to the CNS of the immune cells, such as T cells, and their progeny prior to clonal expansion. In some embodiments, the immune cells, such as T cells, are genetically modified to block the trafficking to the CNS of the immune cells, such as T cells, and their progeny after to clonal expansion.

The cell donor may be the individual to whom the expanded population of cells will be administered, i.e. an autologous cell donor. Alternatively, the immune cells, such as T cells, may be obtained from a cell donor that is a different individual from the individual to whom the immune cells, such as T cells, will be administered, i.e. an allogenic cell. If an allogenic cell is used, it is preferred that the cell donor be type matched, that is identified as expressing the same or nearly the same set of leukocyte antigens as the recipient.

Immune cells, such as T cells, may be obtained from a cell donor by routine methods including, for example, isolation from blood fractions, particularly the peripheral blood monocyte cell component, or from bone marrow samples.

Once immune cells, such as T cells, are obtained from the cell donor, one or more T cells may be transformed with a nucleic acid that encodes a T cell receptor that recognizes at least one epitope of an intestinal antigen or transformed with a nucleic acid that encodes a T cell receptor that recognizes at least one epitope of a CNS antigen, either before or after modification of immune cells, such as T cells, to block trafficking to the intestine or CNS, respectively.

The nucleic acid molecule that encodes the cell receptor that recognizes at least one epitope of either an intestinal antigen or a CNS antigen may be obtained by isolating a T cell that recognizes at least one epitope of either an intestinal antigen or CNS antigen from a "TCR gene donor" who has T cells that express a T cell receptor that recognizes at least one epitope of an intestinal antigen or T cells that express a T cell receptor that recognizes at least one epitope of an intestinal antigen, respectively. Such TCR gene donors may have T cells that recognize at least one epitope of either an intestinal antigen or CNS antigen due to an immune response that arises from exposure to an immunogen other than by vaccination or, such TCR gene donors may be identified as those who have received a vaccine which induces production of T cells that recognize at least one epitope of an intestinal antigen or T cells that recognize at least one epitope of a CNS antigen, i.e. a vaccinated TCR gene donor The vaccinated TCR gene donor may have been previously vaccinated or may be administered a vaccine specifically as part of an effort to generate such T cells that recognize at least one epitope of either an intestinal antigen or CNS antigen for use in a method that comprises transforming T cells with a nucleic acid molecule that encodes a T cell receptor that recognizes at least one epitope of either an intestinal antigen or CNS antigen, expanding the cell number, and administering the expanded population of transformed T cells to an individual. As noted above, the T cells may genetically modified to block the trafficking to the intestine or CNS, respectively, prior to transforming them, after transforming them, prior to clonal expansion or after clonal expansion.

The TCR gene donor may be the individual who will be the recipient of the transformed T cells or a different individual from the individual who will be the recipient of the transformed T cells. The TCR gene donor may be same individual as the cell donor or the TCR gene donor may be a different individual than the cell donor. In some embodiments, the cell donor is the recipient of the transformed T cells and the TCR gene donor is a different individual. In some embodiments, the cell donor is the same individual as the TCR gene donor and is a different individual from the recipient of the transformed T cells. In some embodiments, the cell donor is the same individual as the TCR gene donor and the same individual as the recipient of the transformed T cells.

Examples of vaccines that used may be used to induce T cells that comprise a T cell receptor which recognizes at least one epitope of an intestinal antigen include those disclosed herein and those disclosed in the patents and published patent applications that have been incorporated by reference herein. Examples of vaccines that used may be used to induce T cells that comprise a T cell receptor which recognizes at least one epitope of a CNS antigen include those disclosed herein and those disclosed in the patents and published patent applications that have been incorporated by reference herein.

The nucleic acid molecule that encodes the T cell receptor that recognizes at least one epitope of either an intestinal antigen or a CNS antigen, i.e. the TCR coding sequence, may be a DNA or RNA molecule. The nucleic acid molecule may be operably linked to the regulatory elements necessary for expression of the TCR coding sequence in a donor T cell. In some embodiments, the nucleic acid molecule that comprises a TCR coding sequence is a plasmid DNA molecule. In some embodiments, the nucleic acid molecule that comprises a TCR coding sequence is a plasmid DNA molecule that is an expression vector wherein the TCR coding sequence is operably linked to the regulatory elements in the plasmid that are necessary for expression of the TCR coding sequence in a donor T cell. In some embodiments, a nucleic acid molecule that comprises a TCR coding sequence may be incorporated into viral particle which is used to infect a donor T cell. Packaging technology for preparing such particles is known. The TCR coding sequence incorporated into the particle may be operable linked to regulatory elements in the plasmid that are necessary for expression of the TCR coding sequence in a donor T cell. In some embodiments, the nucleic acid molecule that comprises a TCR coding sequence is incorporated into a viral genome. In some embodiments, the viral genome is incorporated into viral particle which is used to infect a donor T cell. Viral vectors for delivering nucleic acid molecules to cells are well known and include, for example, viral vectors based upon vaccine virus, adenovirus, adeno associated virus, pox virus as well as various retroviruses. The TCR coding sequence incorporated into the viral genome may be operable linked to regulatory elements in the plasmid that are necessary for expression of the coding sequence in a donor T cell.

Upon expression of the nucleic acid in the transformed immune cells, such as T cells, the transformed cells may be tested to identify a immune cells, such as T cells, that recognizes at least one epitope of either an intestinal antigen or a CNS antigen. Such transformed immune cells, such as T cells, may be identified and isolated from the sample using standard techniques. The protein that comprises at least one epitope of either an intestinal antigen or a CNS antigen may be adhered to a solid support and contacted with the sample. Immune cells, such as T cells, that remain on the surface after washing are then further tested to identify immune cells, such as T cells, that which recognize at least one epitope of either an intestinal antigen or a CNS antigen. Affinity isolation methods such as columns, labeled protein that binds to the cells, cell sorter technology may also be variously employed. T cells that recognize at least one epitope of either an intestinal antigen or a CNS antigen may also be identified by their reactivity in the presence of a protein with at least one epitope of either an intestinal antigen or a CNS antigen.

Once an immune cell, such as a T cell, is identified as a cell that recognizes at least one epitope of either an intestinal antigen or a CNS antigen, it may be clonally expanded using tissue culture techniques with conditions that promote and maintain cell growth and division to produce an exponential number of identical cells. The expanded population of immune cells, such as T cells, may be collected for administration to a patient. Prior to administration of such T cells to patients, the immune cells, such as T cells, are genetically modified to block trafficking to sites that express the antigen. That is, prior to administration of anti-intestinal antigen immune cells, such as T cells, to patients, the immune cells, such as T cells, are genetically modified to block trafficking to sites that express the intestinal antigen; prior to administration anti-CNS antigen immune cells, such as T cells, to patients, the immune cells, such as T cells, are genetically modified to block trafficking to sites that express the CNS antigen.

In some embodiments, the immune cells, such as T cells, are genetically modified to block the trafficking of the immune cells, such as T cells, and their progeny to the intestine prior to transformation with a nucleic acid molecule that encodes a T cell receptor which recognizes at least one epitope of an intestinal antigen. In some embodiments, the immune cells, such as T cells, are genetically modified to block the trafficking of the immune cells, such as T cells, and their progeny to the intestine after transformation with a nucleic acid molecule that encodes a T cell receptor which recognizes at least one epitope of an intestinal antigen. In some embodiments, the immune cells, such as T cells, are genetically modified to block the trafficking of the immune cells, such as T cells, and their progeny to the CNS prior to transformation with a nucleic acid molecule that encodes a T cell receptor which recognizes at least one epitope of a CNS antigen. In some embodiments, the immune cells, such as T cells, are genetically modified to block the trafficking of the immune cells, such as T cells, and their progeny to the CNS after transformation with a nucleic acid molecule that encodes a T cell receptor which recognizes at least one epitope of a CNS antigen. In some embodiments, the immune cells, such as T cells, are genetically modified to block the trafficking of the immune cells, such as T cells, and their progeny to the intestine prior to clonal expansion. In some embodiments, the immune cells, such as T cells, are genetically modified to block the trafficking of the immune cells, such as T cells, and their progeny to the intestine after clonal expansion. In some embodiments, the immune cells, such as T cells, are genetically modified to block the trafficking of the immune cells, such as T cells, and their progeny to the CNS prior to clonal expansion. In some embodiments, the immune cells, such as T cells, are genetically modified to block the trafficking of the immune cells, such as T cells, and their progeny to the CNS after clonal expansion. Examples of vaccines and vaccination methods that used may be used to induce immune cells, such as T cells, that comprise a T cell receptor which recognizes at least one epitope of an intestinal antigen include those disclosed herein and those disclosed in the patents and published patent applications that have been incorporated by reference herein.

T Cells Transformed with CARs

A plurality of immune cells, such as T cells, which recognize at least one epitope of either an intestinal antigen or a CNS antigen may be obtained by isolating an immune cell such as a T cell from a cell donor, transforming it with either a nucleic acid molecule that encodes either an intestinal antigen-binding membrane-bound CAR, or a CNS antigen-binding membrane-bound CAR and, culturing the transformed cell to exponentially expand the number of transformed immune cells, such as T cells, to produce a plurality of such cells.

The cell donor may be the individual to whom the expanded population of cells will be administered, i.e. an autologous cell donor. Alternatively, the immune cell such as a T cell may be obtained from a cell donor that is a different individual from the individual to whom the immune cells, such as T cells, will be administered, i.e. an allogenic cell. If an allogenic cell is used, it is preferred that the cell donor be type matched, that is identified as expressing the same or nearly the same set of leukocyte antigens as the recipient.

Immune cells such as T cells may be obtained from a cell donor by routine methods including, for example, isolation from blood fractions, particularly the peripheral blood monocyte cell component, or from bone marrow samples.

Once immune cells, such as T cells, are obtained from the cell donor, one or more immune cells, such as T cells, may be transformed with either a nucleic acid molecule that encodes either an intestinal antigen-binding CAR or a CNS antigen-binding CAR.

The nucleic acid molecule that encodes either the intestinal antigen-binding CAr or the CNS antigen-binding CAR may be obtained by isolating a B cell that produces antibodies that recognize at least one epitope of either an intestine antigen or a CNS antigen, respectively, from an "antibody gene donor" who has such B cells that produce antibodies that recognizes at least one epitope of either an intestine antigen or a CNS antigen, respectively. Such antibody gene donors may have B cells that produce antibodies that recognize at least one epitope of either an intestine antigen or a CNS antigen, respectively, due to an immune response that arises from exposure to an immunogen other than by vaccination or, such antibody gene donors may be identified as those who have received a vaccine which induces production of B cells that produce antibodies that recognize at least one epitope of either an intestine antigen or a CNS antigen, respectively, i.e. a vaccinated antibody genetic donor The vaccinated antibody genetic donor may have been previously vaccinated or may be administered a vaccine specifically as part of an effort to generate such B cells that produce antibodies that recognize at least one epitope of either an intestine antigen or a CNS antigen, respectively, for use in a method that comprises transforming immune cells, such as T cells, with a nucleic acid molecule that encodes either an intestinal antigen-binding membrane-bound fusion protein or a CNS antigen-binding membrane-bound fusion protein, expanding the cell number, and administering the expanded population of transformed immune cells, such as T cells, to an individual.

The antibody gene donor may be the individual who will be the recipient of the transformed immune cells, such as T cells, or a different individual from the individual who will be the recipient of the transformed immune cells, such as T cells. The antibody gene donor may be same individual as the cell donor or the antibody gene donor may be a different individual than the cell donor. In some embodiments, the cell donor is the recipient of the transformed immune cells, such as T cells, and the antibody gene donor is a different individual. In some embodiments, the cell donor is the same individual as the antibody gene donor and is a different individual from the recipient of the immune cells, such as T cells. In some embodiments, the cell donor is the same individual as the antibody gene donor and the same individual as the recipient of the transformed immune cells, such as T cells.

Examples of vaccines that used may be used to induce B cells that produce antibodies which recognize at least one epitope of either an intestine antigen or a CNS antigen, respectively, include those disclosed herein and those disclosed in the patents and published patent applications that have been incorporated by reference herein. The nucleic acid molecule which encodes either an intestinal antigen-binding CAR or a CNS antigen-binding CAR comprises a coding sequence that encodes functional binding fragment of an antibody that recognizes at least one epitope of an intestinal antigen or a CNS antigen, respectively, linked to a signaling moiety. The coding sequences are linked so that they encode a single product that is expressed.

The coding sequence that encodes a functional binding fragment of an antibody that recognizes at least one epitope of either an intestinal antigen or a CNS antigen may be isolated from a B cell from an antibody gene donor. Such a B cell may be obtained and the genetic information isolated. In some embodiments, the B cells are used to generate hybrid cells which express the antibody and therefore carry the antibody coding sequence. The antibody coding sequence may be determined, cloned and used to make the CMA-binding membrane-bound fusion protein. A functional binding fragment of an antibody that recognizes at least one epitope of either an intestinal antigen or a CNS antigen may include some or all of the antibody protein which when expressed in the transformed T cells retains its binding activity for at least one epitope of either an intestinal antigen or a CNS antigen, respectively.

The coding sequences for a protein sequence that provides for the expressed the signally moiety may be any protein which can signal activation of immune cells as described above.

The nucleic acid molecule that encodes either an intestinal antigen-binding CAR or a CNS antigen-binding CAR may be a DNA or RNA molecule. The nucleic acid molecule may be operably linked to the regulatory elements necessary for expression of the coding sequence in a donor immune cell such as a T cell. In some embodiments, the nucleic acid molecule that encodes either an intestinal antigen-binding CAR or a CNS antigen-binding CAR is a plasmid DNA molecule. In some embodiments, the nucleic acid molecule that encodes either an intestinal antigen-binding CAR or a CNS antigen-binding CAT is a plasmid DNA molecule that is an expression vector wherein the coding sequence is operably linked to the regulatory elements in the plasmid that are necessary for expression of the either intestinal antigen-binding CAR or CNS antigen-binding CAR in a donor immune cell such as a T cell. In some embodiments, a nucleic acid molecule that comprises either an intestinal antigen-binding CAR coding sequence or a CNS antigen-binding CAR coding sequence may be incorporated into viral particle which is used to infect a donor cell. Packaging technology for preparing such particles is known. The coding sequence incorporated into the particle may be operable linked to regulatory elements in the plasmid that are necessary for expression of the either intestinal antigen-binding CAR coding sequence or a CNS antigen-binding CAR coding sequence in a donor T cell. In some embodiments, the nucleic acid molecule that comprises either an intestinal antigen-binding CAR coding sequence or a CNS antigen-binding CAR coding sequence is incorporated into a viral genome. In some embodiments, the viral genome is incorporated into viral particle which is used to infect a donor cell. Viral vectors for delivering nucleic acid molecules to cells are well known and include, for example, viral vectors based upon vaccine virus, adenovirus, adeno-associated virus, pox virus as well as various retroviruses. The coding sequence incorporated into the viral genome may be operable linked to regulatory elements in the plasmid that are necessary for expression of the coding sequence in a donor cell.

Upon expression of the nucleic acid in the transformed immune cells such as T cells, the transformed cells may be tested to identify a cell that recognizes at least one epitope of either an intestinal antigen or CNS antigen. Such transformed cells may be identified and isolated from the sample using standard techniques. The protein that comprises at least one epi tope of an intestinal antigen or CNS antigen, respectively, may be adhered to a solid support and contacted with the sample. Immune cells, such as T cells, that remain on the surface after washing are then further tested to identify cells that which recognize at least one epitope of either intestinal antigen or CNS antigen. Affinity isolation methods such as columns, labeled protein that binds to the cells, cell sorter technology may also be variously employed. cells that recognize at least one epitope of intestinal antigen or CNS antigen may also be identified by their reactivity in the presence of a protein with at least one epitope of intestinal antigen or CNS antigen.

Once an immune cell such as a T cell is identified as a cell that recognizes at least one epi tope of either intestinal antigen or CNS antigen, it may be clonally expanded using tissue culture techniques with conditions that promote and maintain cell growth and division to produce an exponential number of identical immune cells, such as cells. The expanded population of immune cells, such as T cells, may be collected for administration to a patient. Prior to administration of such immune cells, such as T cells, to patients, the immune cells, such as T cells, are genetically modified to block trafficking to sites that express the antigen. That is, prior to administration of anti-intestinal antigen immune cells, such as T cells, to patients, the immune cells, such as T cells, are genetically modified to block, trafficking to sites that express the intestinal antigen; prior to administration of anti-CNS antigen immune cells, such as T cells, to patients, the immune cells, such as T cells, are genetically modified to block trafficking to sites that express the CNS antigen.

In some embodiments, the immune cells, such as cells, are genetically modified to block the trafficking of the immune cells, such as T cells, and their progeny to the intestine prior to transformation with intestinal antigen-binding CAR coding sequence. In some embodiments, the T cells are genetically modified to block the trafficking of the immune cells, such as T cells, and their progeny to the intestine after transformation with intestinal antigen-binding CAR coding sequence. In some embodiments, the immune cells, such as T cells, are genetically modified to block the trafficking of the immune cells, such as T cells, and their progeny to the CNS prior to transformation CNS antigen-binding CAR coding sequence. In some embodiments, immune cells, such as T cells, are genetically modified to block the trafficking of the immune cells, such as T cells, and their progeny to the CNS after transformation with CNS antigen-binding CAR coding sequence. In some embodiments, the immune cells, such as T cells, are genetically modified to block the trafficking of the immune cells, such as T cells, and their progeny to the intestine prior to clonal expansion. In some embodiments, immune cells, such as T cells, are genetically modified to block the trafficking of the immune cells, such as T cells, and their progeny to the intestine after clonal expansion. In some embodiments, the immune cells, such as T cells, are genetically modified to block the trafficking of the immune cells, such as T cells, and their progeny to the CNS prior to clonal expansion. In some embodiments, the immune cells, such as T cells, are genetically modified to block the trafficking of the immune cells, such as T cells, and their progeny to the CNS after clonal expansion. Examples of vaccines and vaccination methods that used may be used to induce immune cells, such as T cells, that comprise a T cell receptor which recognizes at least one epitope of an intestinal antigen include those disclosed herein and those disclosed in the patents and published patent applications that have been incorporated by reference herein.

Modifications to Block Trafficking

The safety of targeted immune cells, such as T cells, can be improved by blocking expression or binding activity of proteins expressed by immune cells, such as T cells, which are known to bind to proteins expressed by normal intestinal or CNS cell types, immune cells, such as T cells, that express $\alpha_4\beta_7$ integrin and chemokine receptor 9 (CCR9) bind cells that express their ligands, MAdCAM-1 and CCL25, respectively. These ligands are expressed by normal intestinal cells and immune cells, such as T cells, that express $\alpha_4\beta_7$ integrin and chemokine receptor 9 (CCR9) are trafficked toward and among such cells that express MAdCAM-1 and CCL25. Thus immune cells, such as T cells, that express $\alpha_4\beta_7$ integrin and chemokine receptor 9 (CCR9) are trafficked toward and among intestinal cells. Similarly, immune cells, such as T cells, that express $\alpha_4$ integrins bind cells that express the ligands of such $\alpha_4$ integrins. Normal CNS cells express ligands of $\alpha_4$ integrins and immune cells, such as T cells, that express $\alpha_4$ integrins are trafficked toward and among such cells that express the ligand. Thus immune cells, such as T cells, that express $\alpha_4$ integrins are trafficked toward and among CNS cells.

T cells express antigen specific receptors (TCRs) which specifically recognize and target the T cells to cells that present antigens recognized by the TCRs. As discussed above, T cells comprise TCRs which render them capable of recognizing a specific antigen. Nucleic acid molecules that encode TCRs that recognize specific antigens can be isolated from one T cell and introduced into others, thereby rendering the recipient cell as being capable of recognizing a specific antigen. Immune cells, such as T cells can also be engineered to target to cells that express a specific antigen by transforming the immune cells such as T cell with a nucleic acid sequence that encodes a CAR which binds to a specific antigen. When the transformed immune cells, such as T cells, expresses the CAR which binds to a specific antigen, the engineered immune cells, such as T cells, will specifically bind to cells displaying the specific antigen.

T cells that target specific antigens may be particularly useful to kill cancer cells that express the specific antigen. Antigen specific T cells have been shown to be effective in treating cancer that has cancer cells express the specific antigen. If the antigen specific T cell binds to a specific antigen expressed by normal cells as well as cancer cells, it is undesirable to expose the normal cells to the T cells. Thus, when a T cell that binds to a specific antigen expressed by normal cells as well as cancer cells also includes proteins that traffick the T cell toward and among normal cells that express the specific antigen, the trafficking proteins bring the T cells toward and among the cells that express the specific antigen. To reduce the likelihood of T cell that binds to a specific antigen expressed by normal cells as well as cancer cells being trafficked toward and among normal cells that express the specific antigen recognized by the T cell, suppressing expression or binding activity of proteins involved in trafficking reduce the likelihood and incidence of the T cells being exposed to the normal cells that express the specific antigen recognized by the T cells.

For example, T cells which recognize intestinal antigens, such as guanylyl cyclase C, sucrase isomaltase, CDX1, or CDX2, are useful to eliminate cancer cells that express such antigens. Thus, the T cells are useful to treat most colorectal cancer, many esophageal cancers, many stomach cancers and a host of other cancers which can be tested and identified as expressing the intestinal antigen such as guanylyl cyclase C, sucrose isomaltase, CDX1, or CDX2. Those skilled in the art can readily test samples of cancer to determine if it expresses an intestinal antigen such as guanylyl cyclase C, sucrase isomaltase, CDX1, or CDX2 and therefore can be treated with T cells that specifically recognize the intestinal antigen. If the T cells that specifically recognize the intestinal antigen express $\alpha_4\beta_7$ integrin and/or chemokine receptor 9 (CCR9), they will be trafficked to cells that express ligands of these proteins. Cells that express ligands of $\alpha_4\beta_7$ integrin and chemokine receptor 9 (CCR9), i.e. cells that express MAdCAM-1 and CCL25, include intestinal cells. Accordingly, T cells that specifically recognize an intestinal antigen and that express $\alpha_4\beta_7$ integrin and/or chemokine receptor 9 (CCR9), will be trafficked toward and among normal intestinal cells due to the expression by the T cell of $\alpha_4\beta_7$ integrin and/or CCR9. The T cells that specifically recognize an intestinal antigen and that are trafficked toward and among normal intestinal cells will bind to normal intestinal cells with resulting undesirable effects. Similarly, CNS cells express ligands of $\alpha_4$ integrins. T cells that specifically recognize a CNS antigen and that express $\alpha_4$ integrins will be trafficked to normal CNS cells and there binding to such normal CNS cell will have undesirable effect.

To reduce the possibility of unwanted side effect by the use of immune cells such as T cells that specifically recognize an intestinal antigen to treat cancers that express such antigens, the expression or binding activity of $\alpha_4\beta_7$ integrin and/or chemokine receptor 9 (CCR9) in such immune cells such as T cells can be inhibited and the reduction in undesirable effects achieved. To reduce the possibility of unwanted side effect by the use of immune cells such as T cells that specifically recognize a CNS antigen to treat cancers that express such antigens, the expression or binding activity of $\alpha_4$ integrins in such immune cells such as T cells can be inhibited and the reduction in undesirable effects achieved.

Inhibition of the expression or binding activity of $\alpha_4\beta_7$ integrin and/or chemokine receptor 9 (CCR9) in immune cells such as T cells or inhibition of the expression or binding activity of $\alpha_4$ integrins in immune cells such as T cells can be achieved through a number of different approaches well known to those skilled in the art. The methods described herein refer to clonal expansion of immune cells, such as T cell populations, by culturing the cells in vitro. The in vitro culturing the immune cells, such as T cells provides the opportunity to use well establish molecular biology techniques of genetic cloning and transfection to introduce nucleic molecules into the cultured cells. Thus, problems common to methods which require in vivo gene delivery are avoided.

Inhibition of the expression of $\alpha_4\beta_7$ integrin and/or chemokine receptor 9 (CCR9) in immune cells such as T cells or inhibition of the expression of $\alpha_4$ integrins in immune cells such as cells can be achieved through a number of different gene silencing approaches which involve routine introduction of nucleic acid molecules into cells being cultured in vitro as in some of the instant methods described herein. Examples of gene silencing include the use of RNA interference (RNAi) using small interfering RNA siRNA and/or microRNA, or the use of antisense technology. Nucleic acid molecules may be introduced into the immune cells such as T cells being cultured in vitro. The nucleic acid molecules may be designed to produce within the cell the siRNA, microRNA or antisense molecules that will result in the inhibition of expression of $\alpha_4\beta_7$ integrin or chemokine receptor 9 (CCR9) or $\alpha_4$ integrins. In the case of $\alpha_4\beta_7$ integrin expression inhibition, it is possible to prevent expression of active $\alpha_4\beta_7$ integrin by silencing the $\alpha_4$ subunit of the $\alpha_4\beta_7$ integrin heterodimer, by silencing the $\beta_7$ subunit of the $\alpha_4\beta_7$ integrin heterodimer, or by silencing both subunits.

Inhibition of the $\alpha_4\beta_7$ integrin and/or chemokine receptor 9 (CCR9) or $\alpha_4$ integrin binding activity in immune cells such as T cells can be achieved through a number of approaches in which nucleic acid molecules that encode proteins which interfere with $\alpha_4\beta_7$ integrin or CCR9 or $\alpha_4$ integrin binding to its ligand. As above, the nucleic acid molecules may be introduced into the immune cells such as T cells being cultured in vitro using well known techniques.

Examples of inhibiting $\alpha_4\beta_7$ integrin binding activity in immune cells such as T cells that express $\alpha_4\beta_7$ integrin include introducing into the immune cells such as T cells nucleic acid sequences that encode decoy molecules which bind to $\alpha_4\beta_7$ integrin at the site of or near $\alpha_4\beta_7$ integrin binding site of its ligand MAdCAM-1. Such decoy molecules prevent the $\alpha_4\beta_7$ integrin from binding to its ligand by occupying the binding site to otherwise interfering with the $\alpha_4\beta_7$-MAdCAM-1 binding by its own binding to $\alpha_4\beta_7$ integrin. Another example provides nucleic acid sequences that encode anti-$\alpha_4\beta_7$ integrin antibodies which may be whole antibodies or $\alpha_4\beta_7$ integrin binding antibody fragments. The antibody-encoding sequences are expressed in the cell and bind to the $\alpha_4\beta_7$ integrin, resulting in the rendering of the $\alpha_4\beta_7$ integrin as unable to bind to MAdCAM-1. In another example, nucleic acid sequences that express negative mutant form of $\alpha_4$ of $\alpha_4\beta_7$ integrin that binds to $\beta_7$ to produce an inactive integrin and/or nucleic acid sequences that express negative mutant form of $\beta_7$ of $\alpha_4\beta_7$ integrin that binds to $\alpha_4$ to produce an inactive integrin and/or both are provided. The expression of the negative mutant result in formation of heterodimers which do not bind to MAdCAM-1. Nucleic acid sequences that encode a protein that competitive forms heterodimers with $\alpha_4$ of $\alpha_4\beta_7$ integrin to dimerize with $\beta_7$ and produce non-$\alpha_4\beta_7$ integrin heterodimers may be provided, nucleic acid sequences that encode a protein that competitive forms heterodimers with $\beta_7$ of $\alpha_4\beta_7$ integrin to dimerize with $\alpha_4$ and produce non-$\alpha_4\beta_7$ integrin heterodimers may be provided or both may be provided. Further nucleic acid sequences that encode MAdCAM-1 which binds to $\alpha_4\beta_7$ integrin may be introduced into the cell whereby the $\alpha_4\beta_7$ integrin-MAdCAM-1 complex forms within the cell, making the $\alpha_4\beta_7$ integrin unavailable for binding to MAdCAM-1 expressed by intestinal cells.

Examples of inhibiting CCR9 binding activity in cells that express CCR9 include introducing into the cells nucleic acid sequences that encode decoy molecules which bind to CCR9 at the site of or near CCR9's binding site of its ligand CCL25. Such decoy molecules prevent CCR9 from binding to CCL25 by occupying the binding site to otherwise interfering with the CCR9 CCL25 binding by its own binding to CCR9. Another example provides nucleic acid sequences that encode anti-CCR9 antibodies which may be whole antibodies or CCR9-binding antibody fragments. The antibody-encoding sequences are expressed in the cell and bind to CCR9, resulting in the rendering of the CCR9 as unable to bind to CCL25. Further nucleic acid sequences that encode CCL25 which binds to CCR9 may be introduced into the cell whereby the CCR9-CCL25 complex forms within the cell, making the CCR9 unavailable for binding to CCL25 expressed by intestinal cells.

Examples of inhibiting $\alpha_4$ integrins binding activity in cells that express $\alpha_4$ integrins include introducing into the cells nucleic acid sequences that encode decoy molecules which bind to $\alpha_4$ integrins at the site of or near $\alpha_4$ integrin binding site of its ligand. Such decoy molecules prevent the $\alpha_4$ integrin from binding to its ligand by occupying the binding site to otherwise interfering with the $\alpha_4$ integrin—Ligand binding by its own binding to $\alpha_4$ integrin. Another example provides nucleic acid sequences that encode anti-$\alpha_4$ integrin antibodies which may be whole antibodies or $\alpha_4$ integrin binding antibody fragments. The antibody-encoding sequences are expressed in the cell and bind to the $\alpha_4$ integrin, resulting in the rendering of the $\alpha_4$ subunit of $\alpha_4$ integrin as unable to form heterodimers. In another example, nucleic acid sequences that express negative mutant form of the $\alpha_4$ subunit of $\alpha_4$ integrin to produce an inactive integrin. The expression of the negative mutant result in formation of heterodimers which do not bind to the ligand of the $\alpha_4$ integrin. Nucleic acid sequences that encode a protein that competitive forms heterodimers with $\alpha_4$ of $\alpha_4$ integrin to prevent dimerization of $\alpha_4$ subunit and produce heterodimers that have reduced binding or do not bind to CNS cells may be provided. Further nucleic acid sequences that encode the $\alpha_4$ integrin's ligand may be introduced into the cell whereby the $\alpha_4$ integrin-ligand complex forms within the cell, making the $\alpha_4$ integrin unavailable for binding to its lingand cells.

Vaccines

Vaccines may be used to induce an immune response against one or more epitopes of intestinal antigen or CNS antigen and produce TCR gene donors and/or donors of B cells useful to make either intestinal antigen-binding membrane-bound fusion protein or CNS antigen-binding membrane-bound fusion protein. A CD4+ helper epitope is provided to induce a broad based immune response. Examples of vaccines include, but are not limited to, the following vaccine technologies:

1) infectious vector mediated vaccines such as recombinant adenovirus, vaccinia, poxvirus, AAV, Salmonella, and BCG wherein the vector carries genetic information that encodes an intestinal antigen or CNS antigen, such that when the infectious vector is administered to an individual, the protein is expressed and a broad based immune response is induced that targets the intestinal or CNS antigen;

2) DNA vaccines, i.e. vaccines in which DNA that encodes an intestinal antigen or CNS antigen, such that when the infectious vector is administered to an individual, the protein is expressed and a broad based immune response is induced that targets the intestinal antigen or CNS antigen, 3) killed or inactivated vaccines which a) comprise either killed cells or inactivated viral particles that display an intestinal antigen or CNS antigen, and b) when administered to an individual induces an immune response that targets the intestinal antigen or CNS antigen;

4) haptenized killed or inactivated vaccines which a) comprise either killed cells or inactivated viral particles that display intestinal antigen or CNS antigen, b) are haptenized to be more immunogenic and c) when administered to an individual induces an immune response that targets the intestinal antigen or CNS antigen;

5) subunit vaccines which are vaccines that comprise intestinal antigen or CNS antigen; and 6) haptenized subunit vaccines which are vaccines that a) include an intestinal antigen or CNS antigen, and b) are haptenized to be more immunogenic.

Intestinal Antigens

Some examples of intestinal antigens are cellular proteins include, but are not limited to, normally colorectal specific proteins such as guanylyl cyclase C, CDX-1, CDX-2, sucrase isomaltase; Villin, A33, Lactase, H(+)/peptide cotransporter 1 (PEPT1, SLC15A1); Intectin; and Carbonic anhydrase.

Treatment Methods

Aspects of the disclosure include methods of treating individuals who have intestinal cancer or CNS cancer. The treatment is provided systemically. An individual is administered a plurality of immune cells, such as T cells that recognize at least one epitope of an intestinal antigen or CNS antigen as set forth herein. The treatment may be adjuvant therapeutic treatment provided together with the ordinary treatment upon diagnosis of intestinal cancer or CNS cancer. One skilled in the art can diagnose intestinal cancer or CNS cancer. The immune cells, such as T cells, are administered in a therapeutically effective amount. The term "therapeutically effective amount" refer to an amount sufficient to reduce or ameliorate symptoms, or reduce the size or eliminate tumors, or inhibit or otherwise slow down growth of tumors compared to that which would occur in the absence of therapeutic treatment.

Prophylactic Methods

The plurality of immune cells, such as T cells that recognize at least one epitope of an intestinal cancer antigen or CNS cancer antigen, may also be used prophylactically in individuals who are at risk of developing intestinal cancer or CNS cancer. There are several ways of identifying individuals who are at elevated or particularly high risk relative to the population. Risk of some cancers can be predicted based upon family history and/or the presence of genetic markers. Certain behaviors or exposure to certain environmental factors may also place an individual into a high risk population. Previous diagnosis with primary disease which has been removed or in remission places the individual at higher risk. Those skilled in the art can assess the risk of an individual and determine whether or not they are at an elevated or high risk of mucosal tissue derived cancer.

Individuals who are at risk of developing as intestinal cells cancer or CNS cancer may be administered a prophylactically effective amount of a plurality of immune cells, such as T cells that recognize at least one epitope of an intestine cancer antigen or CNS cancer antigen prior to the individual having detectable disease. The term "prophylactically effective amount" refers to an amount sufficient to reduce the incidence of cancer compared that which would occur in the absence of prophylactic treatment.

Compositions, Formulations, Doses and Regimens

A plurality of immune cells, such as T cells, according to some embodiments comprise a pharmaceutically acceptable carrier in combination with the cells. Pharmaceutical formulations comprising cells are well known and may be routinely formulated by one having ordinary skill in the art. Suitable pharmaceutical carriers are described in Remington's Pharmaceutical. Sciences, A. Osol, a standard reference text in this field, which is incorporated herein by reference. The present disclosure relates to pharmaceutical composition for infusion.

In some embodiments, for example, the plurality of cells can be formulated as a suspension in association with a pharmaceutically acceptable vehicle. Examples of such vehicles are water, saline, Ringer's solution, dextrose solution, and 5% human serum albumin. The vehicle may contain additives that maintain isotonicity (e.g., sodium chloride, mannitol) and chemical stability (e.g., buffers and preservatives). The vehicle is sterilized prior to addition of cells by commonly used techniques.

The plurality of cells may be administered by any means that enables them to come into contact with cancer cells. Pharmaceutical compositions may be administered intravenously for example.

Dosage varies depending upon the nature of the plurality of cells, the age, health, and weight of the recipient; nature and extent of symptoms, kind of concurrent treatment, frequency of treatment, and the effect desired. Generally $1 \times 10^{10}$ to $1 \times 10^{12}$ cells are administered although more or fewer may also be administered, such as $1 \times 10^9$ to $1 \times 10^{13}$. Typically, $1 \times 10^{11}$ cells are administered. The amount of cells delivered is the amount sufficient to induce a protective or therapeutically response. Those having ordinary skill in the art can readily determine the range and optimal dosage by routine methods.

The patents, published patent applications and references cited throughout this disclosure are hereby incorporated herein by reference.

The following example is provided as an exemplary embodiment only and is not intended to limit the scope of the disclosure.

EXAMPLE

Example 1

T cells may be harvested from PBMCs of colorectal cancer patients by leukapheresis or from tumor infiltratin lymphocytes (TILs) of colorectal cancer patients. TIL explants or PBMC-derived T cells will be cultured in complete medium (RPM11640 based medium supplemented with 10% human serum) containing 6000 of IL-2. The cultures may be maintained at cell concentrations between $5 \times 10^5$ and $2 > 10^6$ cells per ml until several million TIL cells are available, usually 2-4 weeks. Multiple independent cultures may be screened by cytokine secretion assay for recognition of epitopes of an intestinal cancer antigen or CNS cancer antigen (target antigen). Two to six independent TIL cultures exhibiting the highest cytokine secretion may be further expanded in complete medium with 6000 IU per ml IL-2 until the cell number is over $5 \times 10^7$ cells (this cell number is typically reached 3-6 weeks after tumor excision).

Employing genetic modification of specific immune cells, such as T cells, inhibit their toxicity can be achieved as follows. Mechanisms of T cell homing (trafficking) to intestine are well established. Intestinal homing relies primarily on interactions between the adhesion molecule $\alpha_4\beta_7$ integrin and the chemokine receptor 9 (CCR9) on T cells and their respective ligands MAdCAM-1 and CCL25 on intestinal endothelium (Snook, A. E., et al., Clin Pharmacol Ther, 2007. 82(6): p. 734-9).

It has been demonstrated that blockade of $\alpha_4$ integrins using the monoclonal antibody natalizumab (Tysabri®) improves disease in Crohn's disease (Gordon, F. H., et al., Gastroenterology, 2001. 121(2): p. 268-74) and multiple sclerosis patients. However, because this treatment blocks all cells from entering the tissue, not just those causing pathology, this drug also increases patient susceptibility to opportunistic infection (Weissert, R., Progressive multifocal leukoencephalopathy, J Neuroimmunol, 2010). Natalizumab as well as other monoclonal antibody therapies are also associated with Immune Reconstitution. Inflammatory Syndrome (IRIS) following cessation of monoclonal antibody therapy. Therefore, while drugs like natalizumab may reduce the severity of autoimmunity associated with adoptive transfer of cells specific to intestinal antigens, it may also result in other toxicities.

Thus, specific blockade of $\alpha_4\beta_7$ and/or CCR9 in GCC-specific T cells by expression of siRNA, decoy, dominant negative, etc molecules allows their transfer to patients with metastatic colorectal cancer without risk of colitis. When targeting other antigens expressed by intestines, such as CEA, CDX2, sucrose isomaltase, etc. specific blockade of $\alpha_4\beta_7$ and/or CCR9 by expression of siRNA, decoy, dominant negative, etc molecules would also allow their transfer to patients with metastatic colorectal cancer without risk of colitis.

Targeting antigens expressed by CNS tissues, through blockade of $\alpha_4$ integrins in T cells may be undertaken. While this is the same target as natalizumab, it will not be associated with the same adverse events, because only the adoptively transferred cells are blocked from entering CNS or intestine above. The patient's endogenous cells will have full access to all tissues, allowing resistance to opportunistic infection, while the adoptively transferred cells will be blocked, preventing adverse side effects.

Because the adoptively transferred T cells will come from one of three sources—1) endogenous T cells with antigen-specific cell receptors, expanded and reintroduced to the patient; 2) T cells engineered to express antigen-specific T cell receptor via gene therapy; or 3) T cells engineered to express antigen-specific chimeric cell receptor utilizing antibody-derived antigen recognition domains via gene therapy—that all involve ex vivo manipulation and reintroduction, an opportunity exists to introduce genetic modification to block these homing molecules alone, or introduce this blockade in combination with antigen-specific receptors. Similarly, other immune cells, such as NK cells, can be identified and cultured.

Reduced dose-limiting toxicity associated with adoptive T cell transfer may be provided. For examples, adoptive transfer of GCC-specific T cells with reduced toxicity may be provided. Similarly, adoptive transfer of T cells specific for other anigens such as CEA, CDX2, sucrose isomaltase, etc may be provided with reduced toxicity.

TIL cultures that maintained target antigen recognition will be expanded for treatment using one cycle of a rapid expansion protocol with irradiated allogeneic feeder cells, OKT3 (anti-CD3) antibody, and 6000 IU per ml IL-2. This rapid expansion protocol typically results in 1000-fold expansions of cells by the time of administration 14-15 days after initiation of the expansions. Patients may receive a bolus intravenous infusion of $1\times10^{11}$ cells over a 0.5 to 1 hour period.

Example 2

T cells for engineering may be obtained from PBMCs following leukopherises by culturing cells at a concentration of $1\times106$/ml in T-cell culture medium AIM-V (Invitrogen Corp, Grand Isle, N.Y.) with 300 IU/ml IL-2, 100 U/ml penicillin, 100 µg/ml streptomycin, 1.25 µg/ml amphotericin, 10 µg/ml ciprofoloxicin, and 5% human AB serum supplemented with 50 ng/ml OKT3. After 2 days of culture, cells will be collected, resuspended in fresh T cell culture medium without OKT3. A retroviral vector (such as pMSGV1) expressing either CMA-specific TCR $\alpha$ and $\beta$ chains or a CMA-binding membrane bound fusion protein using a Murine Stem Cell Virus (MSCV) long terminal repeat (LTR) and a highly efficient internal ribosome entry site (IRES) derived from the human polio virus (for TCR only). A clinical grade retroviral vector supernatant will be commercially produced and used in a solid-phase transduction protocol that results in highly efficient gene transfer without the use of any selection method. The transduction of up to $5\times10^8$ cells will be performed by overnight culture on Retronectin (CH-296, GMP grade Retronectin purchased from Takara Bio. Inc, Japan) coated, vector-preloaded six well tissue culture plates, using 6 ml vector and up to $5\times10^6$ cells per well. Patients will receive a bolus intravenous infusion of $1\times10^{10}$-$10^{11}$ cells over a 0.5 to 1 hour period.

Example 3

T cells will be expanded above from PBMCs or TILs. RNA isolated from a target antigen specific T-cell clone will be subjected to RACE (rapid amplification of cDNA ends) polymerase chain reaction (PCR) and DNA sequence analysis in order to determine TCR $\alpha$ and $\beta$ chain usage to design PCR primers for cloning of the individual chain full-length cDNAs. PolyA+ RNA will be isolated from the T cells using the Poly (A) Pure mRNA purification kit (Ambion, Austin, Tex.). Reverse transcription-polymerase chain reaction (RT-PCR) was performed using the Titan One Tube RT-PCR kit (Roche, Indianapolis, Ind.) using pairs of oligonucleotide primers for the rearranged $\alpha$ and $\beta$ TCR chains. The amplified products will be gel purified and cloned into the retroviral vector backbone. Cloned $\alpha$ and $\beta$ segments will be confirmed by sequencing.

Example 4

Target antigen specific B cell hybridomas may be produced. Mice may be immunized with target antigen to produce a target antigen specific B cell (antibody) response. Spleens will be collected to harvest antibody producing B cells. These will be fused with the SP2/0-Ag14 myeloma cell line using a methylcellulose-based medium system, ClonaCell-HY Monoclonal Antibody Production Kit (StemCell Technologies, Inc). Fused cells will be cloned by limiting-dilution and screened for target antigen specific antibody production to identity target antigen specific producing hybridomas. These will be maintained as a permanent source of target antigen specific monoclonal antibody.

The heavy and light-chain antibody sequence will be cloned from the selected hybridoma to generate a scFV (single-chain Fv) antibody by PCR. cDNA will be produced from the hybridoma RNA using degenerate oligonucleotides (oligodT). The VL and VH (heavy and light-chain variable segments) will be amplified and assembled into the scFV using a three-step PCR approach with established oligonucleotides. The scFV produced from the CMA-specific hybridoma will be used to produce a chimeric antigen receptor (CMA-binding membrane-bound fusion protein or T-body).

The CAR/T-body genes will be of the tripartite configuration in which a target antigen specific scFv will be linked by PCR through the CD28 extracellular domain (from which the ligand-binding region was truncated) to the intracellular part of the FcRIγ chain. The T-body cDNA construct will be cloned into the retroviral vector and used to transfect T cells to produce T-body-expressing T cells for therapy.

Example 5

Transfer may be combined with various treatments including cytokine administration (primarily IL-2), target antigen-directed vaccination and/or antibody therapy, chemotherapy, host preparative lymphodepletion with cyclophosphamide and fludarabine total-body irradiation (TBI), among other potential adjunct treatments.

Some embodiments disclosed in PCT/US10/053733 provide isolated pluralities of T cells which recognize at least one epitope of guanylyl cyclase C (GCC), pharmaceutical compositions comprising such isolated plurality of T cells and methods of making such pluralities of T cells. Some such methods comprise the steps of isolating a sample from a cell donor that comprises at least one T cell that recognize at least one epitope of GCC; identifying a T cell that recognize at least one epitope of GCC; and culturing said T cell under conditions to promote its replication for a period sufficient to produce a plurality of I cells that recognize at least one epitope of GCC. Other methods comprise the steps of isolating a sample from a cell donor that comprises at least one T cell; transforming the T cell with a nucleic acid sequence that encodes either a cell receptor that recognizes at least one epitope of GCC, or a GCC-binding membrane-bound fusion protein that comprises at least a functional fragment of an antibody that binds to at least one epitope of GCC, wherein upon expression the fusion protein is a membrane bound protein; and culturing transformed T cell under conditions to promote its replication for a period sufficient to produce plurality of T cells that recognize at least one epitope of GCC. Effective amount of pluralities of T cells that recognize at least one epitope of GCC are disclosed for use in methods of treating an individual who has been diagnosed with metastatic colorectal cancer or another primary or metastatic cancer that expresses GCC such as esophageal and stomach cancer as well as in methods of preventing metastatic colorectal cancer or another primary or metastatic cancer that expresses GCC such as esophageal and stomach cancer in an individual identified as being at an elevated risk of developing metastatic colorectal cancer or another primary or metastatic cancer that expresses GCC such as esophageal and stomach cancer. Nucleic acid molecules are disclosed in 61/638,639, which is incorporated herein by reference, which comprise a nucleotide sequence that encodes antibodies that bind to GCC.

Example 6

In some embodiments, anti-GCC CAR designs may comprise a GCC specific scFv will be linked by PCR through the CD28 extracellular domain (from which the ligand-binding region was truncated) to the intracellular part of the FcRIγ chain.

In some embodiments, anti-GCC CAR designs may comprise a GCC specific scFv will be linked by PCR through the CD28 extracellular domain (from which the ligand-binding region was truncated) to the intracellular part of the CD3zeta signaling chain.

In some embodiments, anti-GCC CAR designs may comprise a GCC specific scFv will be linked by PCR through to the intracellular part of the FcRIγ chain.

In some embodiments, anti-GCC CAR designs may comprise a GCC specific scFv will be linked by PCR to the intracellular part of the CD3zeta signaling chain.

REFERENCES

Each of the following patents, published patent applications and publications are hereby incorporated herein by reference in their entirety.

U.S. Pat. Nos. 5,359,046, 5,906,936, 5,912,172, 6,319,494, 6,407,221 and 7,741,465 describes cells and methods of providing cells with chimeric receptor genes which include antibody-derived antigen binding recognition.

U.S. Pat. No. 7,977,095 discloses methods of generating and enriching antigen-specific T cells.

U.S. Pat. No. 7,067,318 discloses methods of transfecting T cells.

U.S. Pat. No. 5,840,301 discloses methods of making single chain antibodies.

PCT/US10/053733.

Brentjens R J, Santos E, Nikhamin Y, Yeh R, Matsushita M, La Perle K, Quintás-Cardama A, Larson S M, Sadelain M. Clin Cancer Res. 2007 Sep. 15;13(18 Pt 1);5426-35. Epub 2007 Sep. 12.

Maher J. Oncol. 2012:278093

Eshhar Z., Handb Exp Pharmacol. 2008;(181):329-42.

Baxevanis C N, Papamichail M. Cancer Immunol Immunother. 2004 October;53(10):893-903. Epub 2004 May 26. Targeting of tumor cells by lymphocytes engineered to express chimeric receptor genes.

Hwu P, Yang J C, Cowherd R, Treisman J, Shafer G E, Eshhar Z, Rosenberg S A., Cancer Res. 1995 Aug. 1;55(15): 3369-73. In vivo antitumor activity of T cells redirected with chimeric antibody/T-cell receptor genes.

D Moritz, V Weis, Mattern, and B Groner, Proc Natl Acad Sci USA. 1994 May 10; 91(10): 4318-4322. Cytotoxic T lymphocytes with a grafted recognition specificity for ERBB2-expressing tumor cells.

Stancovski I, Schindler D G, Waks T, Yarden Y, Sela M, Eshhar Z. J Immunol. 1993 Dec. 1;151(11):6577-82. Targeting of T lymphocytes to Neu/HER2-expressing cells using chimeric single chain Fv receptors.

Haynes N M, Trapani J A, Teng M W, et al. Single-chain antigen recognition receptors that costimulate potent rejection of established experimental tumors. Blood. 2002;100: 3155-63.

Pinthus J H, Waks T, Malina V, et al. Adoptive immunotherapy of prostate cancer bone lesions using redirected effector lymphocytes. J Clin Invest. 2004;114:1774-81.

Patel S D, Ge Y, Moskalenko M, McArthur J G. Anti-Tumor CC49.zeta CD4 T cells possess both cytolytic and helper functions. J Immunother. 2000;23:661-8.

Gade T P, Hassen W, Santos E, et al. Targeted elimination of prostate cancer by genetically directed human T lymphocytes. Cancer Res. 2005;65:9080-8

Haynes N M, Trapani J A, Teng M W, et al. Rejection of syngeneic colon carcinoma by CTLs expressing single-chain antibody receptors codelivering CD28 costimulation. J Immunol. 2002;169:5780-6

Ho W Y, Blattman J N, Dossett M L, Yee C, Greenberg P D. Adoptive immunotherapy: engineering T cell responses as biologic weapons for tumor mass destruction. Cancer Cell. 2003;3:431-7.

Kahlon K S, Brown C, Cooper Li, Raubitschek A, Forman S J, Jensen M C. Specific recognition and killing of glioblastoma multiforme by interleukin 13-zetakine redirected cytolytic T cells. Cancer Res. 2004;64:9160-6.

Kershaw M H, Teng M W, Smyth M J, Darcy P K. Supernatural T cells: genetic modification of T cells for cancer therapy. Nat Rev Immunol. 2005;5:928-40

Ma Q, Safar M, Holmes E, Wang Y, Boynton A L, Junghans R P. Anti-prostate specific membrane antigen designer T cells for prostate cancer therapy. Prostate. 2004; 61:12-25

Mansoor W, Gilliam D E, Thistlethwaite F C, Hawkins R E. Engineering T cells for cancer therapy. Br J Cancer. 2005;93:1085-91.

Rossig C, Brenner M K. Genetic modification of T lymphocytes for adoptive immunotherapy. Mol Ther. 2004; 10:5-18.

R. E. Hawkins, D. E. Gilham, R. Debets, et al., "Development of adoptive cell therapy for cancer: a clinical perspective," Human Gene Therapy, vol. 21, no. 9, pp. 1039-1042, 2010.

Z. Eshhar, "The T-body approach: redirecting T cells with antibody specificity," Handbook of Experimental Pharmacology, no. 181, pp. 329-342, 2008.

J. S. Bridgeman, R. E. Hawkins, A. A. Hombach, H. Abken, and D. E. Gilham, "Building better chimeric antigen receptors for adoptive T cell therapy," Current Gene Therapy, vol. 10, no. 2, pp. 77-90, 2010.

H. M. Finney, A. N. Akbar, and A. D. G. Lawson, "Activation of resting human primary T cells with chimeric receptors: costimulation from CD28, inducible costimulator, CD134, and CD137 in series with signals from the TCRζ chain," The Journal of Immunology, vol. 172, no. 1, pp. 104-113, 2004.

A. Hombach, A Wieczarkowiecz, T. Marquardt et al., "Tumor-specific T cell activation by recombinant immunoreceptors: CD3ζ signaling and CD28 costimulation are simultaneously required for efficient IL-2 secretion and can be integrated into ono combined CD28/CD3ζ signaling receptor molecule," The Journal of Immunology, vol. 167, no. 11, pp. 6123-6131, 2001.

H. J. Lamers, P. van Elzakker, S. C. L. Langeveld, S. Sleijfer, and J. W. Gratama, "Process validation and clinical evaluation of a protocol to generate gene-modified T lymphocytes for imunogene therapy for metastatic renal cell carcinoma: GMP-controlled transduction and expansion of patient's T lymphocytes using a carboxy anhydrase IX-specific scFv transgene," Cytotherapy, vol. 8, no. 6, pp. 542-553, 2006.

A. Tran, L. Burton, D. Russom et al., "Manufacturing of large numbers of patient-specific T cells for adoptive immunotherapy: an approach to improving product safety, composition, and production capacity," Journal of Immunotherapy, vol. 30, no. 6, pp. 644-654, 2007.

S. Masiero, C. Del Vecchio, R. Gavioli et. al, "T-cell engineering by a chimeric T-cell receptor with antibody-type specificity for the HIV-1 gp120," Gene Therapy. vol. 12, no. 4, pp. 299-310, 2005.

Dudley M E, Wunderlich J R, Robbins P F, Yang J C, P, Schwartzentruber D J, Topalian S L, Sherry R, Restifo N P, Hubicki A M, Robinson M R, Raffeld M, Duray P, Seipp C A, Rogers-Freezer L, Morton K E, Mavroukakis S A, White D E, Rosenberg S A. Cancer regression and autoimmunity in patients after clonal repopulation with antitumor lymphocytes. Science 2002; 298:850-4.

Dudley M E, Yang J C, Sherry R, Hughes M S, Royal R, Kammula U, Robbins P F, Huang J, Citrin D E, Leitman S F, Wunderlich J, Restifo N P, Thomasian A, Downey S G, Smith, F O, Klapper J, Morton K, Laurencot C, White D E, Rosenberg S A. Adoptive Cell Therapy for Patients With Metastatic Melanoma: Evaluation of Intensive Myeloablative Chemoradiation Preparative Regimens. J Clin Oncol 2008. 16.5449.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis S A, Rosenberg S A. Cancer regression in patients after transfer of genetically engineered lymphocytes. Science 2006; 314:126-9, Hughes M S, Yu Y Y, Dudley M E, Zheng Z, Robbins P E, Li Y, Wunderlich J, Hawley R G, Moayeri M, Rosenberg S A, Morgan R A. Transfer of a TCR gene derived from a patient with a marked antitumor response conveys highly active T-cell effector functions. Hum Gene Ther 2005; 16:457-72.

Pinthus J H, Waks T, Malina V, Kaufman-Francis K, Hamelin A, Aizenberg I, Kanety H, Ramon J, Eshhar Z. Adoptive immunotherapy of prostate cancer bone lesions using redirected effector lymphocytes. J Clin invest 2004; 114:1774-81.

Yokoyama W M, Christensen M, Santos G D, Miller D. Production of monoclonal antibodies. Curr Protoc Immunol 2006; Chapter 2:Unit 2 5.

Snook A E, Stafford B J, Li P, Tan G, Huang L, Birbe R, Schulz S, Schnell M J, Thakur M, Rothstein J L, Eisenlohr L C, Waldman S A. Guanylyl Cyclase C-Induced immunotherapeutic Responses Opposing Tumor Metastases Without Autoimmunity. J Natl Cancer Inst 2008; 100:950-961.

Irani Y, Tea M, Tilton R G, Coster D J, Williams K A, Brereton H M. PCR amplification of the functional immunoglobulin heavy chain variable gene from a hybridoma in the presence of two aberrant transcripts. J Immunol Methods 2008; 336:246-50.

Laht S, Meerits K, Altroff H, Faust H, Tsaney R, Kogerman P, Jarvekulg L, Paalme V, Valkna A, Timmusk S. Generation and characterization of a single-chain Fv antibody against G, a hedgehog signaling pathway transcription factor. Hybridoma (Larchmt) 2008; 27:167-74.

Nam C H, Moutel S, Teillaud J L. Generation of murine scFv intrabodies from B-cell hybridomas. Methods Mol Biol 2002; 193:301-27.

Eshhar Z, Waks T, Bendavid A, Schindler D G. Functional expression of chimeric receptor genes in human T cells. Journal of Immunological Methods 2001; 248:67-76.

Universal CD4+ helper epitopes, such as PADRE and others are disclosed in U.S. Pat. No. 5,736,142 issued Apr. 7, 1998 to Sette, et al.; U.S. Pat. No. 6,413,935 issued Jul. 2, 2002 to Sette, et al.; and U.S. Pat. No. 7,202,351 issued Apr. 10, 2007 to Sette, et al.

Other peptides reported to bind to several DR types include those described in Busch et al., Int. Immunol. 2, 443-451 (1990); Panina-Bordignon et al., Eur. J. Immunol. 19, 2237-2242 (1989); Sinigaglia et al., Nature 336, 778-780 (1988); O'Sullivan et al., J. Immunol. 147, 2663-2669 (1991) Roache et al., J. Immunol. 144, 1849-1856 (1991); and Hill et al., J. Immunol. 147, 189-197 (1991). Additionally, U.S. Pat. No. 6,413,517 issued Jul. 2, 2002 to Sette, et al. refers to the identification of broadly reactive DR restricted epitopes.

Villin is described in Wang Y, Srinivasan K, Siddiqui M R, George S P, Tomar A, Khurana S. A novel role for villin in intestinal epithelial cell survival and homeostasis. J Biol Chem 2008.

A33 is described in Johnstone C N, White S J, Tebbutt N C, Clay F J, Ernst M, Biggs W H, Viars C S, Czekay S, Arden K C, Heath J K. Analysis of the regulation of the A33 antigen gene reveals intestine-specific mechanisms of gene expression. J Biol Chem 2002;277:34531-9.

Lactase is described in lactase-phlorizin hydrolase) (Lee S Y, Wang Z, Lin C K, Contag C H, Olds L C, Cooper A D, Sibley E. Regulation of intestine-specific spatiotemporal expression by the rat lactase promoter. J Biol Chem 2002; 277:13099-105.

H(+)/peptide cotransporter 1 (PEPT1, SLC15A1) is described in Daniel H. Molecular and integrative physiology of intestinal peptide transport. Annu Rev Physiol 2004;66: 361-84; Terada T, Inui K. Peptide transporters: structure, function, regulation and application for drug delivery. Curr Drug Metab 2004;5:85-94; and Shimakura J, Terada T, Shimada Y, Katsura T, Inui K. The transcription factor Cdx2 regulates the intestine-specific expression of human peptide transporter 1 through functional interaction with Sp1. Biochem Pharmacol 2006;71:1581-8.

Intectin is described in Kitazawa H, Nishihara T, Nambu T, Nishizawa H, Iwaki M, Fukuhara A, Kitamura T, Matsuda M, Shimomura I. Intectin, a novel small intestine-specific glycosylphosphatidylinositol-anchored protein, accelerates apoptosis of intestinal epithelial cells. J Biol Chem 2004; 279:42867-74.

Carbonic anhydrase is described in Drummond F, Sowden J, Morrison K, Edwards Y H. The caudal-type homeobox protein Cdx-2 binds to the colon promoter of the carbonic anhydrase 1 gene. Eur J Biochem 1996; 236:670-81.

The invention claimed is:

1. A plurality of T cells which recognize at least one epitope of guanylyl cyclase C and which are modified to inhibit expression or activity of $\alpha_4\beta_7$ integrin, wherein said T cells are derived from clonal expansion of T cells that are isolated from an individual and transformed with a nucleic acid molecule which encodes a chimeric antigen receptor which binds to guanylyl cyclase C.

2. The plurality of T cells of claim 1 wherein the chimeric antigen receptor that binds to guanylyl cyclase C comprises:
   a guanylyl cyclase C specific scFv linked to a truncated CD28 extracellular domain to the intracellular part of the FcRIγ chain;
   a guanylyl cyclase C specific scFv linked to a truncated CD28 extracellular domain to the intracellular part of the CD3zeta signaling chain;
   a guanylyl cyclase C specific scFv linked to the intracellular part of the FcRIγ chain; or
   a guanylyl cyclase C specific scFv linked to the intracellular part of the CD3zeta signaling chain.

3. The plurality of T cells of claim 1, wherein the plurality of T cells are modified to inhibit expression of $\alpha_4\beta_7$ integrin by providing the plurality of T cells with nucleic acid sequences selected from the group consisting of: nucleic acid sequences that express siRNA which inhibits expression of $\alpha_4\beta_7$ integrin, nucleic acid sequences that express microRNA which inhibits expression of $\alpha_4\beta_7$ integrin, and nucleic acid sequences that express antisense sequences which inhibit expression of $\alpha_4\beta_7$ integrin.

4. The plurality of T cells of claim 1, wherein the plurality of T cells are modified to inhibit activity of $\alpha_4\beta_7$ integrin by providing the plurality of T cells with nucleic acid sequences selected from the group consisting of: nucleic acid sequences that encode decoy molecules which bind to $\alpha_4\beta_7$ integrin at the site $\alpha_4\beta_7$ integrin binds to MAdCAM-1, nucleic acid sequences that encode anti-$\alpha_4\beta_7$ integrin antibodies, nucleic acid sequences that express negative mutant form of $\alpha_4$ of $\alpha_4\beta_7$ integrin that binds to $\beta_7$ to produce an inactive integrin; nucleic acid sequences that express negative mutant form of $\beta_7$ of $\alpha_4\beta_7$ integrin that binds to $\alpha_4$ to produce an inactive integrin; nucleic acid sequences that encode a protein that competitive forms heterodimers with $\alpha_4$ of $\alpha_4\beta_7$ integrin to dimerize with $\beta_7$ and produce non-$\alpha_4\beta_7$ integrin heterodimers; nucleic acid sequences that encode a protein that competitive forms heterodimers with $\beta_7$ of $\alpha_4\beta_7$ integrin to dimerize with $\alpha_4$ and produce non-$\alpha_4\beta_7$ integrin heterodimers; and nucleic acid sequences that encode MAdCAM-1 which binds to $\alpha_4\beta_7$ integrin.

5. A pharmaceutical composition comprising a plurality of T cells of claim 1 and a pharmaceutically acceptable carrier or diluent.

6. A method of treating an individual who has been diagnosed with cancer that expresses guanylyl cyclase C comprising the step of administering to the individual an effective amount of a plurality of T cells of claim 1.

7. The plurality of T cells of claim 2, wherein the plurality of T cells are modified to inhibit expression of $\alpha_4\beta_7$ integrin by providing the plurality of T cells with nucleic acid sequences selected from the group consisting of: nucleic acid sequences that express siRNA which inhibits expression of $\alpha_4\beta_7$ integrin, nucleic acid sequences that express microRNA which inhibits expression of $\alpha_4\beta_7$ integrin, and nucleic acid sequences that express antisense sequences which inhibit expression of $\alpha_4\beta_7$ integrin.

8. The plurality of T cells of claim 2, wherein the plurality of T cells are modified to inhibit activity of $\alpha_4\beta_7$ integrin by providing the plurality of T cells with nucleic acid sequences selected from the group consisting of: nucleic acid sequences that encode decoy molecules which bind to $\alpha_4\beta_7$ integrin at the site $\alpha_4\beta_7$ integrin binds to MAdCAM-1, nucleic acid sequences that encode anti-$\alpha_4\beta_7$ integrin antibodies, nucleic acid sequences that express negative mutant form of $\alpha_4$ of $\alpha_4\beta_7$ integrin that binds to $\beta_7$ to produce an inactive integrin; nucleic acid sequences that express negative mutant form of $\beta_7$ of $\alpha_4\beta_7$ integrin that binds to $\alpha_4$ to produce an inactive integrin; nucleic acid sequences that encode a protein that competitive forms heterodimers with $\alpha_4$ of $\alpha_4\beta_7$ integrin to dimerize with $\beta_7$ and produce non-$\alpha_4\beta_7$ integrin heterodimers; nucleic acid sequences that encode a protein that competitive forms heterodimers with $\beta_7$ of $\alpha_4\beta_7$ integrin to dimerize with $\alpha_4$ and produce non-$\alpha_4\beta_7$ integrin heterodimers; and nucleic acid sequences that encode MAdCAM-1 which binds to $\alpha_4\beta_7$ integrin.

9. A method of treating an individual who has been diagnosed with cancer that expresses guanylyl cyclase C comprising the step of administering to the individual an effective amount of a plurality of T cells of claim 2.

* * * * *